United States Patent [19]

Takahashi et al.

[11] Patent Number: 5,150,234
[45] Date of Patent: Sep. 22, 1992

[54] IMAGING APPARATUS HAVING ELECTROOPTIC DEVICES COMPRISING A VARIABLE FOCAL LENGTH LENS

[75] Inventors: Susumu Takahashi, Kunitachi; Akira Takano; Hirofumi Miyanaga, both of Hachiouji; Hisanari Shimazu, Akishima; Kimihiko Nishioka, Hachiouji; Akitoshi Toda, Kunitachi; Masaru Shiraiwa, Hachiouji; Akira Taniguchi, Hachiouji, all of Japan

[73] Assignee: Olympus Optical Co., Ltd., Tokyo, Japan

[21] Appl. No.: 787,139

[22] Filed: Nov. 4, 1991

Related U.S. Application Data

[62] Division of Ser. No. 390,402, Aug. 7, 1989, Pat. No. 5,071,229.

[30] Foreign Application Priority Data

Aug. 8, 1988 [JP] Japan .................. 63-197733
Oct. 24, 1988 [JP] Japan .................. 63-267612
Jan. 12, 1989 [JP] Japan ...................... 1-5434

[51] Int. Cl.⁵ ............................................. G02F 1/13
[52] U.S. Cl. ............................ 359/65; 359/73; 359/74; 359/84; 359/94; 359/41
[58] Field of Search .............. 359/36, 38, 40, 41, 359/53, 63, 65, 73, 84, 94, 265, 67

[56] References Cited

U.S. PATENT DOCUMENTS

| | | | |
|---|---|---|---|
| 4,037,929 | 7/1977 | Bricot et al. ................ | 359/40 |
| 4,047,847 | 9/1977 | Toda et al. .................. | 359/53 |
| 4,190,330 | 2/1980 | Berreman ................... | 359/46 |
| 4,394,069 | 7/1983 | Kaye ........................... | 359/53 |
| 4,601,545 | 7/1986 | Kern ............................ | 359/94 |
| 4,904,063 | 2/1990 | Okada et al. ................ | 359/40 |
| 4,927,241 | 5/1990 | Kuijk .......................... | 359/94 X |
| 5,071,229 | 12/1991 | Oaki et al. .................. | 359/53 |

FOREIGN PATENT DOCUMENTS

59-156219 10/1984 Japan .
62-35090 7/1987 Japan .

*Primary Examiner*—Stanley D. Miller
*Assistant Examiner*—Huy K. Mai
*Attorney, Agent, or Firm*—Cushman, Darby & Cushman

[57] ABSTRACT

An imaging apparatus is provided with a negative lens, a variable focussing lens unit including a material with an electrooptic effect, a light blocking unit, including the material with the electrooptic effect, capable of changing an aperture diameter, and a switch, interlocked with each other, capable of supplying electric power to the variable focussing lens unit and the light blocking unit which are arranged in order on an optical axis from an object side to an image side. When the switch is turned off, the variable focussing lens unit is set to bring an object at a far point into focus and the light blocking unit is set so that an aperture is determined by an aperture stop, while on the other hand, when the swtich is turned on, the variable focussing lens unit is set so that an object at a near point is in focus and the light blocking unit is set to be smaller in aperture. Apertures different in size are determined by a plurality of annular transparent electrodes incorporated in the light blocking unit and configured concentrically. Thus the imaging apparatus can be constructed to be small or compact in size and is easy in manufacturing.

14 Claims, 14 Drawing Sheets

IMAGING APPARATUS HAVING ELECTROOPTIC DEVICES COMPRISING A VARIABLE FOCAL LENGTH LENS

This is a division of application No. 07/390,402, filed Aug. 7, 1989 now U.S. Pat. No. 5,071,229.

BACKGROUND OF THE INVENTION a) Field of the Invention

The present invention relates to an imaging apparatus having electrooptic devices preferable to endoscopes in which a stop diameter of an imaging lens is changed by interlocking with focusing adjustment of the imaging lens.

b) Description of the Prior Art

An imaging optical system for endoscopes in which a stop diameter of an imaging lens is changed by interlocking with focusing adjustment of the imaging lens has been described in the past in, for example, Japanese Patent Publication No. Sho 62-35090 and Japanese Patent Preliminary Publication No. Sho 63-78119. The optical system described in Sho 62-35090 is adapted to arrange slidably a holding frame for an objective lens provided in a non-flexible distal end portion of an endoscope in a longitudinal direction of the endoscope and interlock a member for limiting the aperture size of an aperture stop provided in the vicinity of the objective lens with the longitudinal movement of the holding frame so that when the holding frame is moved longitudinally by performing operation through an accessible control for focusing adjustment, the aperture size of the stop varies accordingly and as a result, brightness and the depth of field can be controlled automatically in accordance with the distance to an object. Further, the optical system stated in Sho 63-78119 is such that an electrochromic stop variable stepwise in aperture size is used as the aperture stop and the imaging optical system is constructed by combining the stop with a multi-focusing lens different in refracting power in accordance with the aperture size and is disposed in the distal end portion of the endoscope. In such an instance, when the aperture size of the electrochromic stop is changed, the position of a beam of light traversing the multi-focusing lens varies accordingly, with the result that the focal length of the imaging optical system depends on the aperture size and an in-focus position is shifted longitudinally. Thus, brightness and the depth of field can be controlled automatically in accordance with the distance to the object.

In the case of the optical system described in Sho 62-35090, however, it is substantially impossible, in view of a space, to accommodate the aperture stop variable mechanically in aperture size, the moving mechanism of the lens holding frame, and their interlocking mechanism in the non-flexible distal end portion of the endoscope of the distal end portion of a non-flexible endoscope. Further, in Sho 63-78119, problems have been encountered that it is considerably difficult that such a lens with a small diameter as used for the endoscope assumes multi-focus and an extremely small electrochromic stop is hard to make.

Recently, an electrooptic stop apparatus such as a liquid crystal stop has been proposed and such a stop apparatus is advantageous to interlock the focusing adjustment of the imaging lens with the variation of the stop diameter of the imaging lens by the combination with the variable focusing lens such as a liquid crystal lens. A conventional example of the electrooptic stop apparatus is described in Japanese Patent Preliminary Publication No. Sho 59-156219. This conventional example is adapted to dispose closely a plurality of annular transparent electrodes concentric with an optical axis in a liquid crystal cell and supply selectively electric power to the electrodes, thereby changing a light transmitting area or light blocking area of the liquid crystal cell to be used as a variable stop.

Also, in the case of the conventional example in the foregoing, problems have arisen that since each electrode is provided with the connection of a lead wire for power supply, the electrode fails to take a complete annular form and clearance thus occurs between the electrodes adjacent to each other, with the result that light leaks out though the clearance even in a light blocking state. In addition, another problem has also arise that the structure is complicated because the area occupied by the connection must be small to such extent as is possible.

In the case where the liquid crystal lens and the liquid crystal stop mentioned above are incorporated in, for example, an objective optical system of the endoscope, a miniaturized circle less than 10 mm in diameter is required and this has brought about difficulties that the connection protrudes from the peripheral edge of a liquid crystal optical element, with great inconvenience in practical use.

SUMMARY OF THE INVENTION

A primary object of the present invention is to provide an imaging apparatus having electrooptic devices which is favorably usable, compact, easy to make and can interlock with the focusing adjustment of an imaging lens to change the stop diameter of the imaging lens.

Another object of the present invention is to provide an improved structure including transparent electrodes for an imaging lens and a stop apparatus constructed of materials having an electrooptic effect such as liquid crystals and liquid crystal polymer and connections with lead wires for power supply which are used for the preceding imaging apparatus.

Still another object of the present invention is to provide the imaging apparatus of the type which is compact and has high performance.

The imaging apparatus according to the present invention is provided with a variable focal length lens constructed of a material having the electrooptic effect such as liquid crystals, liquid crystal polymer, PLZT, etc., light blocking means variable in aperture size, and means for changing the focal length of the variable focal length lens in synchronization with variation of the aperture size of the light blocking means. Thus, the brightness of visual field and the depth of field according to the focusing and the distance to the object can be controlled.

According to the present invention, the light blocking means comprises a first transparent cell in which a material having the electrooptic effect is enclosed with a transparent electrode configured on the entire surface of one inner side and a transparent electrode configured in a section corresponding to a portion of the circumferential direction of each of a plurality of concentric circle-shaped segments on the other inner side and a second transparent cell in which a material having the electrooptic effect is enclosed that a transparent electrode is configured on the entire surface of one inner side and a transparent electrode is configured in a section corresponding to a portion of the circumferential direction of each of the plurality of concentric circle-shaped segments on the other inner side and covering the portion devoid of the transparent electrode on the other inner side of the first cell. Thus, all the segments assume complete annular forms and the area of the portion where the lead wire for power supply is connected to the transparent electrode can be increased.

According to the present invention, another light blocking means is constructed by laminating a plurality of annular transparent electrodes, through an electrical insulation layer, corresponding to a plurality of concentric circle-shaped segments and coinciding with the peripheral edge of the transparent cell in respect to those of the electrodes. Since a plurality of segments assume complete annular forms and all the electrodes coincide with the peripheral edge of the transparent cell, not only the connection with the lead wire is facilitated, but also the entire light blocking means becomes compact.

Further, according to the present invention, the variable focal length and/or the light blocking means are constructed so that a pair of circular lens elements or a pair of transparent plates having the electrodes are made to face each other through a spacer and the material having the electrooptic effect is enclosed between them, and the connection between the transparent electrode and the lead wire for power supply is configured in a space of a cutting portion provided in at least one of the lens element of the transparent plate and the spacer. Thereby, the variable focal length lens and the light blocking means can be constructed in compact circular forms and easily incorporated as the imaging optical system in the endoscope and the like.

These and other objects as well as the features and the advantage of the present invention will become apparent from the following detailed description of the preferred embodiments when taken in conjunction with the accompanying drawings.

DESCRIPTION OF THE PREFERRED EMBODIMENTS

Figure 1:
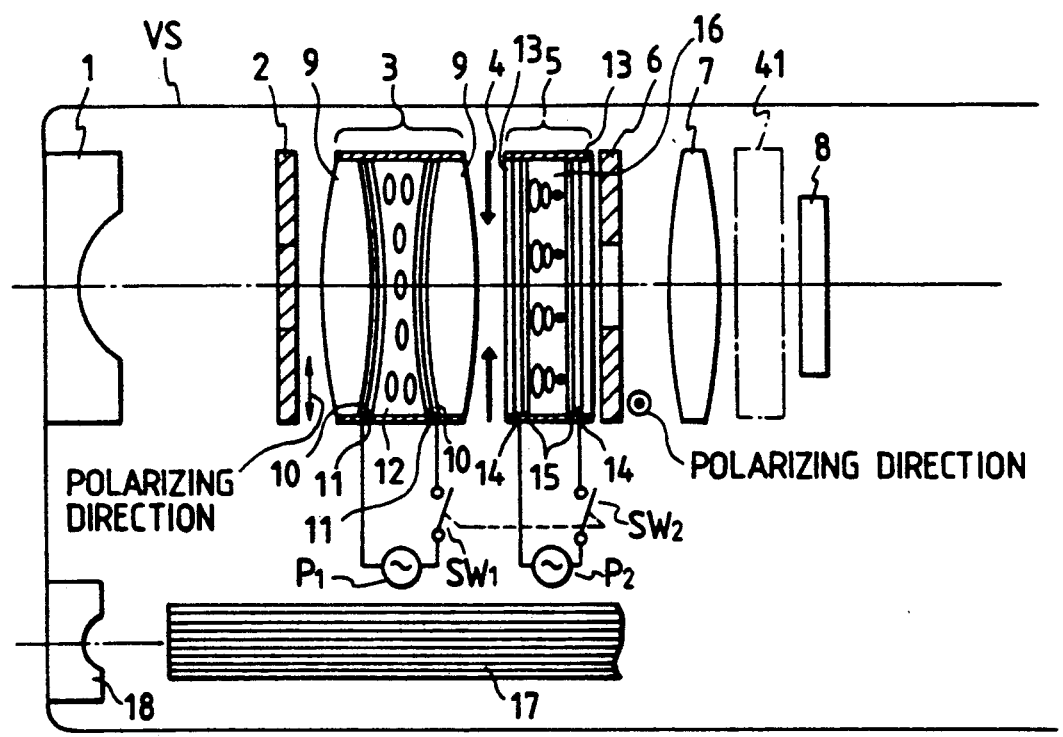
FIGS. 1 and 2 are views showing an in-focus state at a far point and an in-focus state at a near point, respectively, of a first embodiment of an imaging optical system according to the present invention.

FIG. 1 shows a first embodiment of the present invention, which is constructed as an image pickup optical system for electronic endoscopes. On the end face of a distal end portion VS of the endoscope is provided a negative lens 1 also used as a cover glass and at the rear of the negative lens 1 are in turn arranged a polarizing plate 2, variable focal length lens 3 including a molecular liquid crystal as a material having an electrooptic effect, an aperture stop 4, an optically active plate 5, a polarizing plate 6 composed of a peripheral polarization part taking a polarizing direction normal to that of the polarizing plate 2 and a central transparent part of a diameter smaller than the opening of the aperture stop 4, a lens 7, and a solid-state image pickup element 8. The liquid crystal lens 3 is constructed in such a manner that a transparent electrode 10 and an orientation film 11 are covered on each of surfaces opposite to each other, of two lenses 9, 9 made from transparent materials such as glass and acrylic resin and a nematic liquid crystal 12 is enclosed in a negative-lens-shaped cell configured by the opposite surfaces. The optically active plate 5 is constructed in such a manner that a transparent electrode 14 and an orientation film 15 are coated on each of the surfaces, opposite to each other, of two parallel transparent plates 13, 13 made from transparent materials such as glass and acrylic resin and a twisted nematic liquid crystal 16 with an angle of torsion of 90° or 270° in a direction of a longitudinal axis of the liquid crystal molecule is enclosed in a cell formed by the opposite surfaces. Alternating current power sources P1, P2 are connected to the transparent electrodes 10, 10 of the liquid crystal lens 3 and the transparent electrodes 14, 14 of the optically active plate 5 through synchronizing switches $SW_1$, $SW_2$, respectively, and in the case illustrated in FIG. 1 where the switches $SW_1$, $SW_2$ are off and voltages are not applied, molecules of the liquid crystals 12 and 16 exhibit the twist alignment and the homogeneous alignment, that is, the alignment that the direction of the longitudinal axis of the molecule is normal to an optical axis. These components constitute the image pickup optical system.

Also, an illuminating optical system comprising a light guide fiber 17 and an illuminating lens 18 is arranged in parallel with the image pickup optical system.

Since this embodiment is constructed as in the foregoing, light coming from an object, in FIG. 1, traverses the negative lens 1, followed by the polarizing plate 2, and turns to linearly polarized light vibrating in a vertical direction to pass through the liquid crystal lens 3. In this case, the direction of the longitudinal axis of the molecule (i.e., the direction in which refractive index is larger) of the liquid crystal 12 coincides with the direction in which the linearly polarized light vibrates, so that a liquid crystal cell functions as an intensive negative lens and consequently the focal length of the liquid crystal lens 3 is increased, which brings about the state that an object at a far point is in focus as the overall optical system. Next, the linearly polarized light emitted from the liquid crystal lens 3 passes through the aperture stop 4 and, after the vibrating direction of the light is turned by an angle of 90° at the optically active plate 5, the light traverses the polarizing plate 6. Since, in such an instance, the vibrating direction of the linearly polarized light coincides with the polarizing direction of the peripheral polarization part of the polarizing plate 6, the whole of the polarizing plate 6 behaves as a transparent body, resulting in the stat that the F-number of the overall optical system is defined by the opening of the aperture sop 4. The linearly polarized light emanating from the polarizing plate 6 is then formed as an image of the object through the positive lens 7 on the solid-state image pickup element 8.

Figure 2:
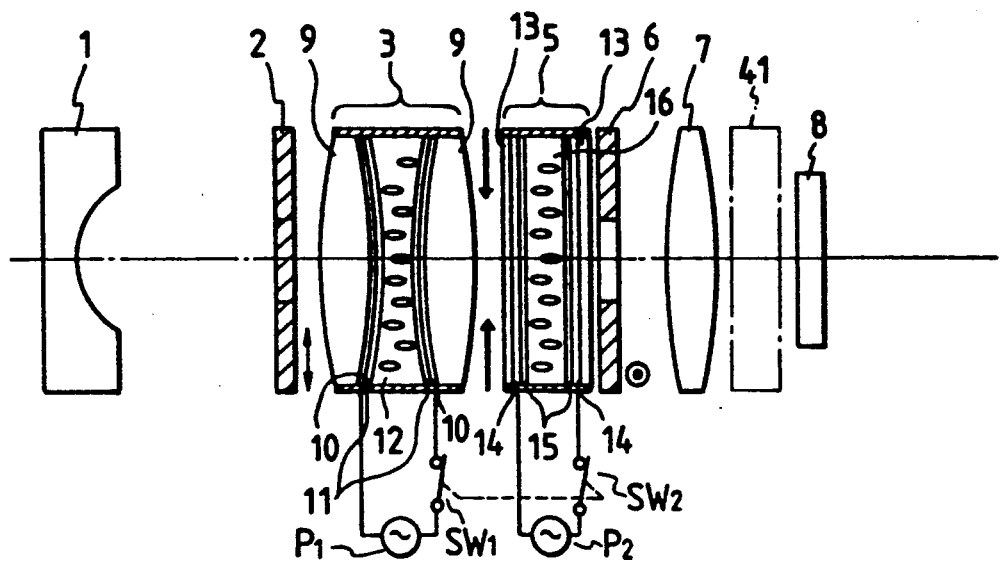

As depicted in FIG. 2, on the other hand, when the switches SW$_1$, SW$_2$ are turned on to apply the voltages, the molecules of the liquid crystals 12 and 16 assume virtually the homeotropic alignment, that is, the alignment that the direction of the longitudinal axis of the molecules is parallel with the optical axis. As a result, the negative lens function of the liquid crystal cell of the liquid crystal lens 3 is weakened, so that the focal length of the liquid crystal lens 3 is reduced, which brings about the state that an object at a near point is in focus as the entire optical system. At the same time, the optical rotatory power of the optically active plate 5 also vanishes, with the result that the vibrating direction of the linearly polarized light traversing the optically active plate 5 is normal to the polarizing direction of the peripheral polarization part of the polarizing plate 6, and the peripheral polarization part behaves as a light blocking part. It follows from this that the linearly polarized light traverses only the central transparent part of the polarizing plate 6 and the F-number of the entire optical system becomes larger, so that the depth of field in the case where the object at the near point is in focus will increase and a picture image with favorable picture quality which is brought into focus will be available.

As is evident from the preceding description, the polarizing plate 2, aperture stop 4, optically active plate 5 and polarizing plate 6 will constitute a light blocking means which can change an aperture to different sizes.

Also, the polarizing plate 2, like the polarizing plate 6, may well be designed so that only its central part is configured with a transparent member (as indicated by dotted lines in FIGS. 1 and 2) and in such a case, it is advantageous that the transmission factor of light increases. However, in the above case, care should be taken because a twin image is caused. Further, in the case where the polarizing plates 2 and 6 are closer to the aperture stop 4, the variation of the F-number relating to an off-axial beam (i.e., shading of the beam) is favorably diminished.

Figure 3:
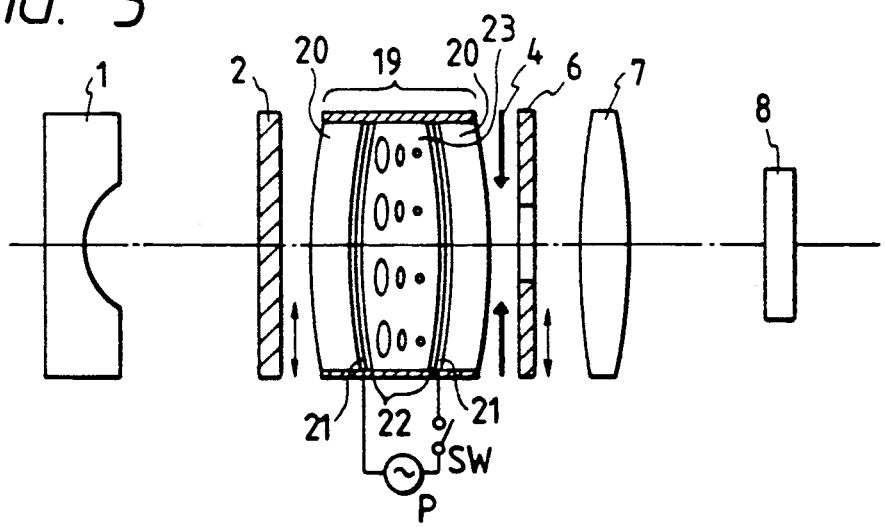
FIGS. 3 and 4 are views showing the in-focus state at a near point and the in-focus state at a far point of a second embodiment, respectively.

FIG. 3 shows a second embodiment constructed as an image pickup optical system for electronic microscopes, which is provided with a double function lens 19 including a molecular liquid crystal exhibiting both the functions of the liquid crystal lens 3 and the optically active plate 5 of the first embodiment. The liquid crystal 19 is constructed in such a manner that a transparent electrode 21 and an orientation film 22 are coated on each of the surfaces of two lenses 20, 20 which are opposite to each other and a twisted nematic liquid crystal 23 with an angle of torsion of 90° or 270° in the direction of the longitudinal axis of the liquid crystal molecule is enclosed in a positive-lens-shaped cell configured by the opposite faces. An alternating current power source P is connected to the transparent electrodes 21, 21 of the liquid crystal lens 19 through a switch SW, and in the case illustrated in FIG. 3 where the switch SW is off and a voltage is not applied, the molecules of the liquid crystal 23 exhibits the twist alignment. Also, the polarizing plates 2 and 6 coincide with each other in polarizing direction.

Since this embodiment is constructed as stated above, light coming from the object, in FIG. 3, travels through the negative lens 1, followed by the polarizing plate 2, and turns to linearly polarized light vibrating in a vertical direction to enter the liquid crystal lens 19. In such an instance, the direction of the longitudinal axis of the molecule of the liquid crystal 23 coincides with the vibrating direction of the linearly polarized light, so that the liquid crystal cell acts as an intensive positive lens and consequently the focal length of the liquid crystal lens 19 is reduced, which brings about the state that an object at a near point is in focus as the entire optical system. Further, after the vibrating direction is turned by 90° a lens 19, the linearly polarized light traverses the polarizing plate 6 through the stop 4. In this case, the vibrating direction of the linearly polarized light is normal to the polarizing direction of the peripheral polarization part of the polarizing plate 6 and therefore the peripheral polarization part acts as a light blocking part. It follows from this that the linearly polarized light traverses only the central transparent part of the polarizing plate 6 and the F-number of the entire optical system becomes larger, so that the depth of field in the case where the object at a near point is in focus will increase and the object image formed through the positive lens 7 on the solid-state image pickup element 8 by the linearly polarized light will be brought into focus and have good quality.

Figure 4:
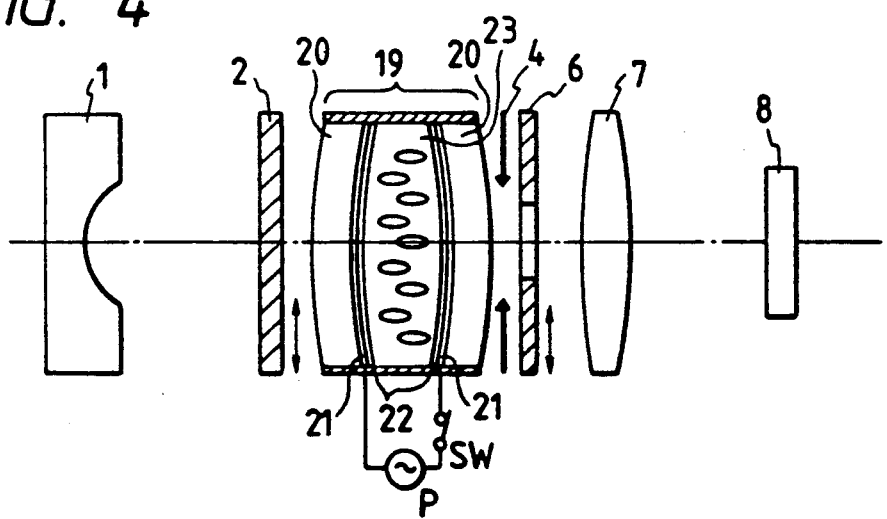

On the other hand, as shown in FIG. 4, when the switch SW is turned on to apply the voltage, the molecules of the liquid crystal 23 change into the homeotropic alignment. Consequently, the positive lens function of the liquid crystal cell of the liquid crystal lens 19 is weakened, so that the focal length of the liquid crystal lens 19 is increased, which brings about the state that the object at a far point is in focus as the entire optical system. At the same time, the optical rotatory power of the liquid crystal lens 19 also vanishes, with the result that the vibrating direction of the linearly polarized light traversing the liquid crystal lens 19 coincides with the polarizing direction of the peripheral polarization part of the polarizing plate 6, and as such the whole of the polarizing plate 6 functions as a transparent body, which increases the amount of light and is favorable for the observation of the object at a far point.

Figure 5:
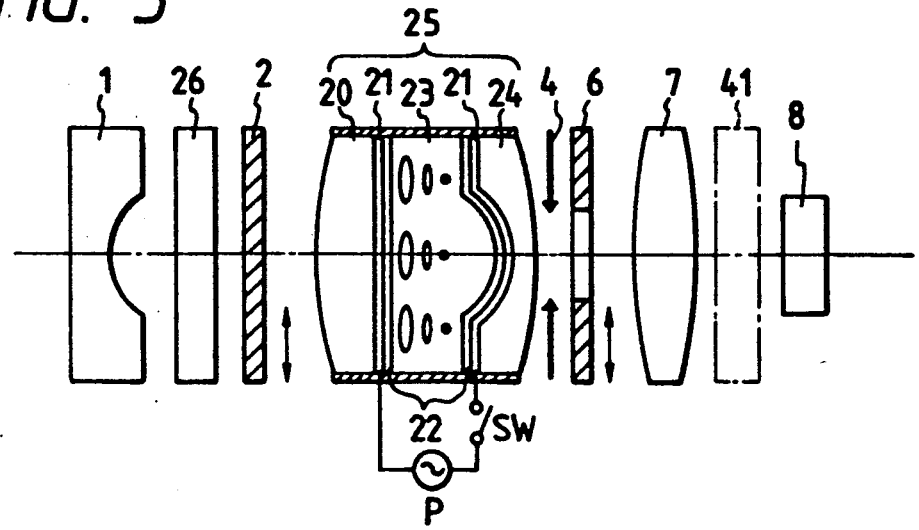
FIGS. 5 and 6 are views showing the in-focus state at a near point and the in-focus state at a far point of a third embodiment, respectively.

FIG. 5 depicts a third embodiment, which has the same arrangement as the second embodiment, except that a liquid crystal lens 25 is used, instead of the liquid crystal lens 19 of the second embodiment, in which a rear lens 24 has the refractive index coinciding with one (lower refractive index in the figure, that is, the refractive index relating to an ordinary ray) of refractive indices for birefringence of the liquid crystal 23 and in which the liquid crystal cell has the configuration that its peripheral part is flat and central part is curved (convex in the figure), and an absorption type infrared light blocking filter 26 composed of glass absorbing infrared light and the like is disposed between the positive lens 1 and the polarizing plate 2. Hence, in the case where the voltage is not applied as shown in FIG. 5, since the linearly polarized light (extraordinary ray) travelling through the peripheral part of the liquid crystal lens 25 is blocked at the peripheral polarization part of the polarizing plate 6 and the linearly polarized light (ordinary ray) traversing the central part is subjected to a strong refractive action at the curved surface to pass through the central transparent part of the polarizing plate 6, it follows that the object at a near point is in focus and the depth of field is increased.

Figure 6:
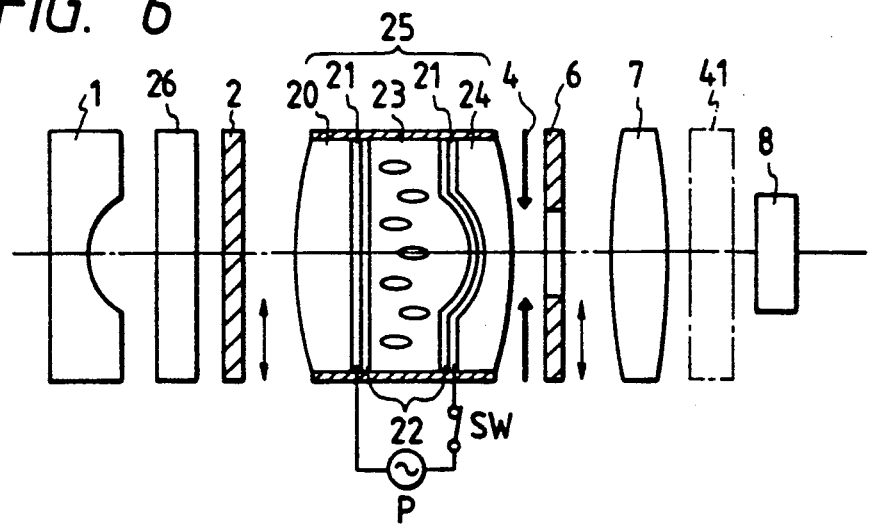

On the other hand, in the state that the voltage is applied as shown in FIG. 6, the linearly polarized light traversing the liquid crystal lens 25 passes through the entire polarizing plate 6 and exhibits refractive characteristics corresponding to the ordinary ray, so that the light is not subjected to the refractive action at the interface between the liquid crystal cell and the lens 24 and consequently the liquid crystal lens 25 turns weak in power as a whole and fails to assume a double focus lens. Thus, the object at a far point is brought into focus and a bright image is attained without any out-of-focus.

This embodiment can bring about strong power even if the center thickness of the liquid crystal cell of the liquid crystal lens 25 is the same in comparison with the second embodiment, and therefore has the advantage that a wide focus adjusting range is available. Further, the infrared light blocking filter 26, which is of the absorption type, possesses the advantage that flare is less than that of an interference type which is provided with a multilayer interference film on, for example, a glass plate to eliminate the infrared light by means of reflection.

Figure 7A:
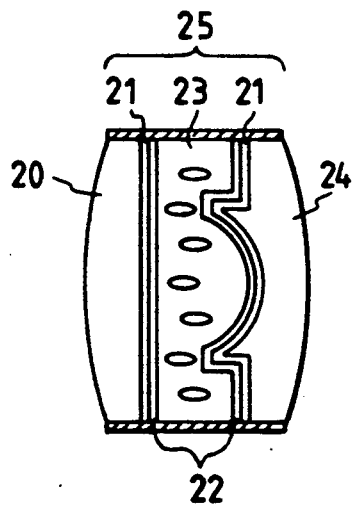
FIGS. 7A and 7B are views showing modified examples of the third embodiment.
Figure 7B:
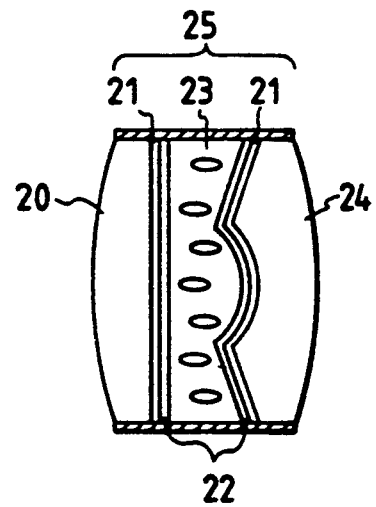

Also, the lens 24 of the liquid crystal lens 25 may well be configured as illustrated in FIGS. 7A and 7B for its modified examples.

Figure 8:
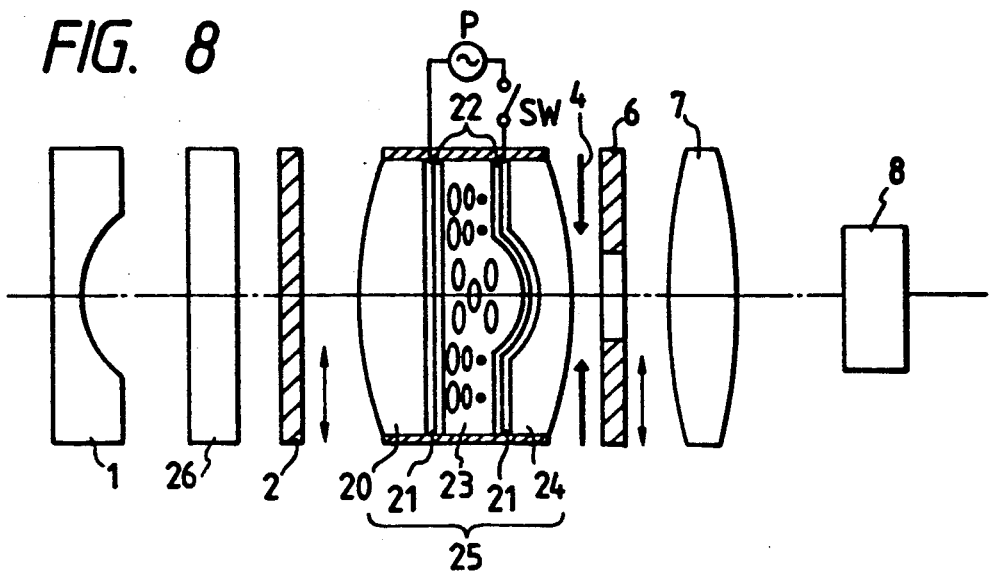
FIG. 8 is a view showing the in-focus state at a near point of a fourth embodiment.

FIG. 8 shows a fourth embodiment, which does not cause the molecules of the liquid crystal 23 at the central curved surface part (positive lens part) of the liquid crystal lens 25 to assume the twist alignment, but mere homogeneous alignment. Specifically, rubbing treatment is applied in such a way that an orientation direction of the orientation film 22 formed on the concave surface of the lens 24 coincides with that of the orientation film 22 on the inside surface of the lens 20 and the orientation direction of the orientation film 22 on the flat surface of the lens 24 makes an angle of 90° with that of the orientation film 22 on the inside surface of the lens 20. This embodiment, therefore, has the advantage that the molecular arrangement of the liquid crystal 23 at the central curved surface part of the liquid crystal lens 25 can easily be controlled.

Also, FIG. 8 shows the state that the voltage is not applied, namely, the object at near point is in focus and, when the voltage is applied, it is to show the state that the object at a far point is in focus like FIG. 6.

Figure 9:
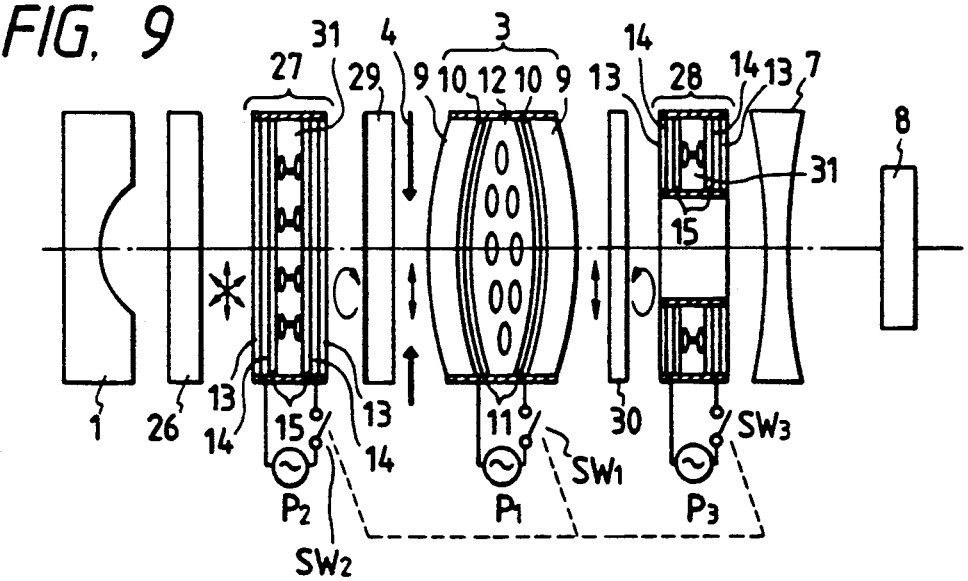
FIGS. 9 and 10 are views showing the in-focus at a near point and the in-focus at far point of a fifth embodiment, respectively.

FIG. 9 depicts a fifth embodiment, which instead of the polarizing plates 2, 6 and the optically active plate 5 of the first embodiment, employs circularly polarizing plates 27, 28 using cholesteric liquid crystals and $\frac{1}{4}$ $\lambda$ plates ($\frac{3}{4}$ $\lambda$ plates and 5/4 $\lambda$ plates available) 29, 30. The circularly polarizing plate 27 is constructed in such a manner that the transparent electrode 14 and the orientation film 15 are covered on each of surfaces, opposite to each other, of two parallel transparent plates 13, 13 and a cholesteric liquid crystal 31 transmitting dextrorotatory circularly polarized light and reflecting levorotatory circularly polarized light is enclosed in a cell formed by the opposite surfaces. The circularly polarizing plate 28 comprises a central part, constructed from a transparent member, of the same element as the circularly polarizing plate 27.

Since this embodiment is constructed as mentioned above, in the case where the voltage is not applied as in FIG. 9, light passing through the negative lens 1 and the infrared light blocking filter 26 is incident on the circularly polarizing plate 27 and then, for example, only the dextro-rotatory circularly polarized light traverses the circularly polarizing plate 27, while the levorotatory circularly polarized light is reflected therefrom. The dextro-rotatory circularly polarized light emanating from the circularly polarizing plate 27 turns to the linearly polarized light through the $\frac{1}{4}$ $\lambda$ plate 29, is subjected to strong positive refraction by the liquid crystal lens 3 assuming the homeotropic alignment, and changes into the levo-rotatory circularly polarized light through the $\frac{1}{4}$ $\lambda$ plate 30 to enter the circularly polarized plate 28. Then, the levo-rotatory circularly polarized light is reflected by the peripheral part of the circularly polarizing plate 28 and travels through only the central part thereof so as to be imaged on the solid-state image pickup element 8 via the negative lens 7. This causes the object at a near point to be in focus and makes the depth of field large.

Figure 10:
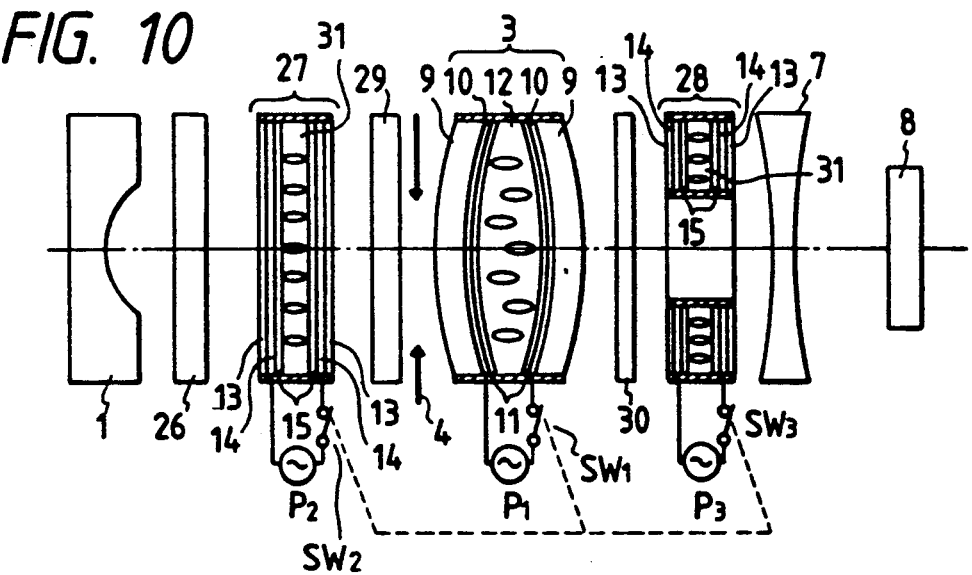

On the other hand, in the case where the voltage is applied as in FIG. 10, due to the liquid crystal 31 whose molecules assume the homeotropic alignment, each of the circularly polarizing plates 27 and 28 is devoid of the selective reflection of the circularly polarized light and serves as a mere transparent plate, with the respect that the light traverses the whole of the circularly polarizing plate 28. Further, since the liquid crystal 12 of the liquid crystal lens 3 turns also to the homeotropic alignment, its refracting action (positive lens action) is weakened and as a result, the object at a far point is brought into focus. Thus, the object at a far point is in focus and a bright image is obtained.

This embodiment is not provided with the polarizing plates in comparison with the first embodiment (refer to FIG. 1), so that the transmittance of light is high and when the object at a far point is in focus, the amount of light of 100% is transmitted with favorable results.

Figure 11:
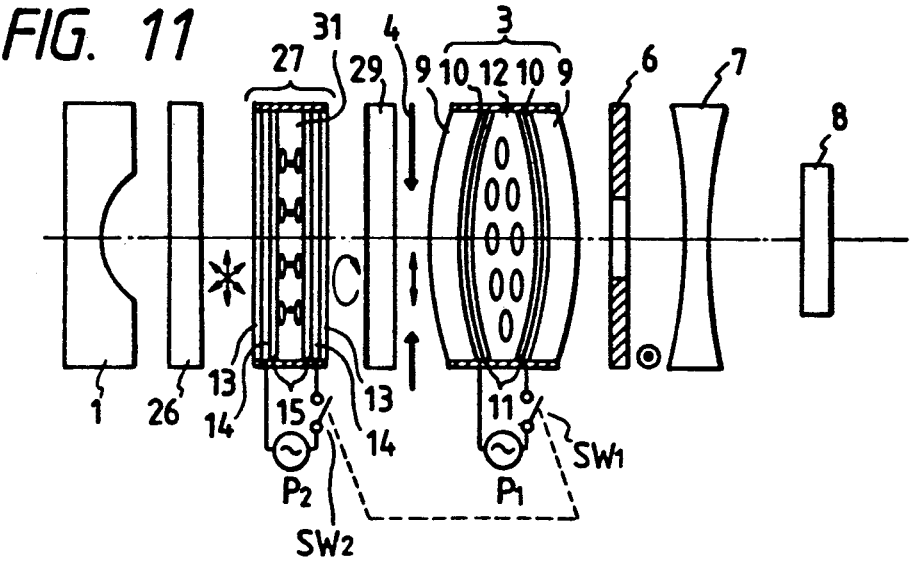
FIG. 11 is a view showing a modified example of the fifth embodiment.

Also, as the modification of the embodiment, the $\frac{1}{4}$ $\lambda$ plate 30 and the circularly polarizing plate 28 may be replaced by the polarizing plate 6 of the first embodiment (refer to FIG. 11). In such a case, a beam of light will be limited when the object at a near point is in focus and light of 50% of the total amount will be transmitted when the object at far point is in focus. This brings about the advantage that the arrangement is simplified because the number of the liquid crystal cells is reduced.

Figure 12:
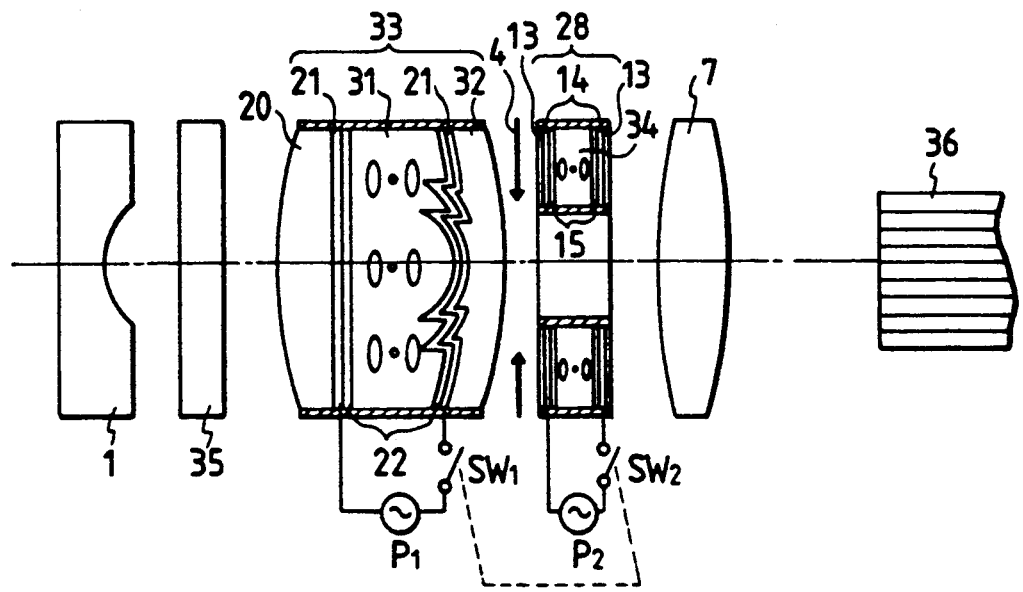
FIGS. 12 and 13 are views showing the in-focus state at a near point and the in-focus state at a far point of a sixth embodiment, respectively.

FIG. 12 shows a sixth embodiment, which has a liquid crystal lens 33 including the cholesteric liquid crystal 31, enclosed therein, transmitting the dextrorotatory circularly polarized light and reflecting the levo-rotatory circularly polarized light and a rear lens 32 as a Fresnel lens, the circularly polarizing plate 28 enclosing a cholesteric liquid crystal 34 transmitting the levo-rotatory circularly polarized light and reflecting the dextrorotatory circularly polarized light, a color filter 35 for correcting coloration caused by the liquid crystal, and an image guide fiber 36. The cholesteric liquid crystal used herein, unlike the nematic liquid crystal, have each the refractive index of a predetermined value with respect to the circularly polarized light. It is common that this value is higher (has an optically negative characteristic) in the case where the cholesteric liquid crystal assumes a layer spiral alignment than in the case where the spiral linkage is released into the homeotropic alignment.

This embodiment is constructed as in the foregoing, so that in the state that no voltage is applied as depicted in FIG. 12, light passing through the negative lens 1 and the color filter 35 is incident on the liquid crystal lens 33 and only the dextro-rotatory circularly polarized light traverses the liquid crystal lens 33, whereas the levo-rotatory circularly polarized light is reflected therefrom. The dextro-rotatory circularly polarized light is then reflected from the peripheral part of the circularly polarizing plate 28 and travels through only the central part thereof. Since the direction of the longitudinal axis of the molecule in the liquid crystal 31 of the liquid crystal lens 33 is normal to the optical axis, the dextrorotatory circularly polarized light is inevitably subjected to strong positive refraction. Consequently, the object at near point will be in focus and the depth of field will be made larger. Also, illuminating light attained by internal illumination such as the light guide like the endoscope is so bright that no trouble arises even if the amount of light is reduced to 50% in the liquid crystal lens 33.

Figure 13:
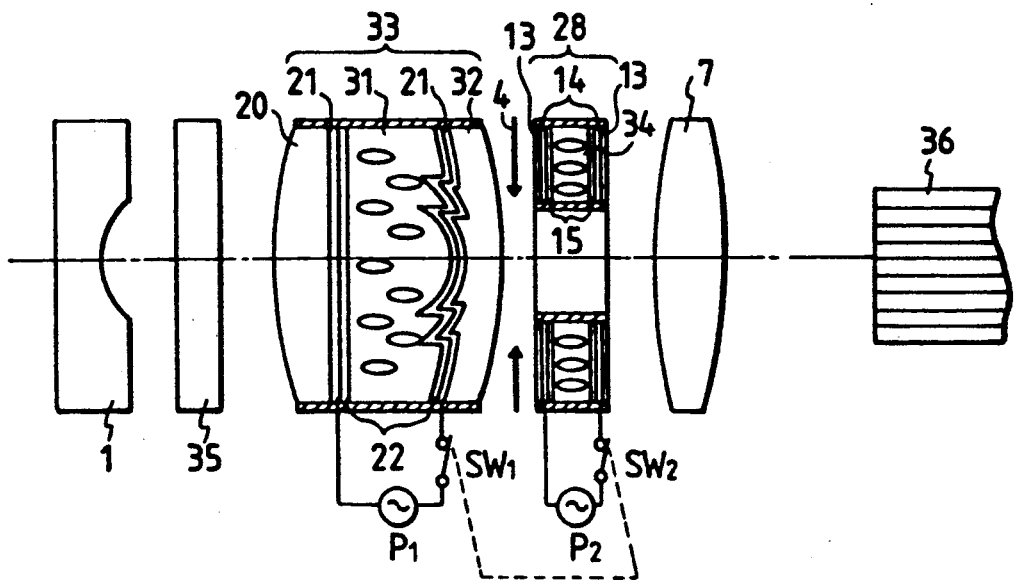

In the case where the voltage is applied as in the FIG. 13, on the other hand, the direction of the longitudinal axis of the molecule in each of the liquid crystals 31 and 34 of the liquid crystal lens 33 and the circularly polarizing plate 28 is parallel to the optical axis, with the result that the liquid crystals are devoid of the selective reflection of the circularly polarized light and the refractive power of the liquid crystal lens 33 is diminished. Thus, the object at a far point will be brought into focus and a bright image will be available.

The embodiment has the advantages that the transmittance of light is higher than in the first embodiment and the arrangement is simple compared with the fifth embodiment. Also, because the rear lens 32 of the liquid crystal lens 33 is configured as the Fresnel lens, the liquid crystal cell is thinner and the results show the advantages that the response to the changeover of the switches SW$_1$, SW$_2$ becomes quick and the loss of light caused by absorption scattering in the liquid crystal layer is diminished. Further, there also is another advantage that since the color filter 35 is placed in front of the liquid crystal lens 33 and the circularly polarizing plate 28, their reflecting light is absorbed to reduce the flare.

The rear lens 32 of the liquid crystal lens 33 may also be an ordinary configuration. In addition, the solid-state image pickup element may well be used in place of the image guide fiber 36.

Figure 14:
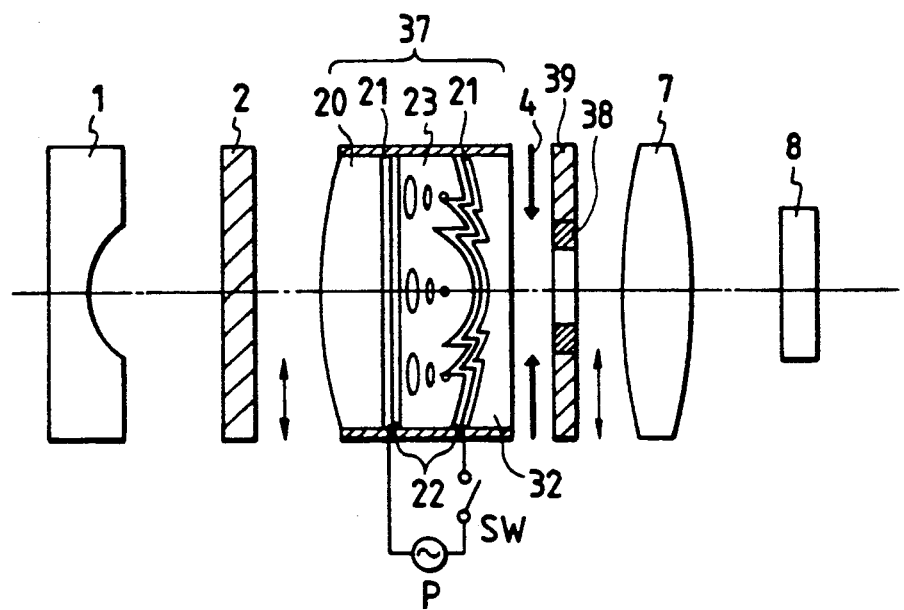
FIG. 14 is a view showing a seventh embodiment.

FIG. 14 shows a seventh embodiment, which employs a liquid crystal lens 37 having the Fresnel type rear lens 32, instead of the liquid crystal lens 19 of the second embodiment, and a polarizing plate 39 having an opaque part 38 in a position corresponding to the Fresnel curved surface connection of the rear lens 32, instead of the polarizing plate 6. As such, since the flare caused by the reflection and refraction generated in all directions at the Fresnel curved surface connection of the rear lens 32 is blocked at the opaque part 38, an ill effect brought about by the flare will be diminished and an image picture with good contrast is available.

Figure 15:
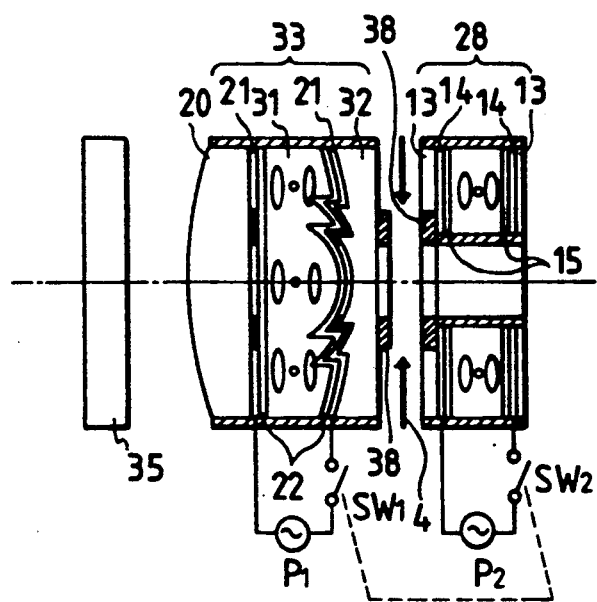
FIG. 15 is a view showing a setting example of an opaque part corresponding to a Fresnel curved surface connection.

Such an arrangement can also be applied to the first embodiment. Also, the opaque part 38, as shown in FIG. 15, may be provided in a portion corresponding to the Fresnel curved surface connection in front of the circularly polarizing plate 28 or in rear of the rear lens 32 of the liquid crystal lens 33, or otherwise may be provided in a portion, corresponding to the Fresnel curved surface connection, of the surface on either side of the transparent electrodes 21, 21 of the front lens 20 or the rear lens 32.

Figure 16:
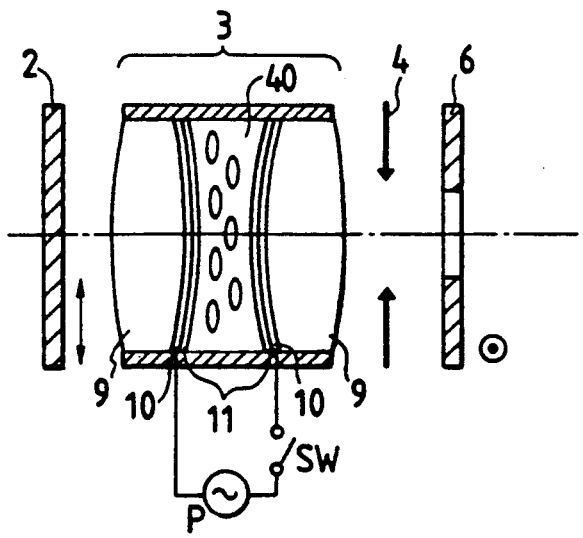
FIGS. 16 and 17 are views showing the in-focus state at a near point and the in-focus state at a far point, respectively, of a modified example of a liquid crystal lens of the first embodiment or the fifth embodiment.
Figure 18:
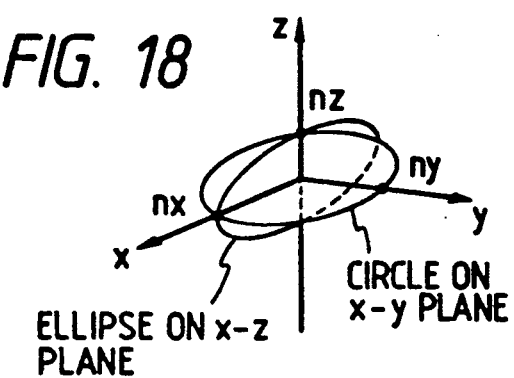
FIG. 18 is a view showing an index ellipsoid.

FIG. 16 shows a modified example of the liquid crystal 3 of the first embodiment or the fifth embodiment (FIG. 9), which makes use of a liquid crystal 40 having a negative birefringent characteristic. The negative birefringent characteristic means $n_z < n_x = n_y$ in an ellipsoid shown in FIG. 18. That is to say, $n_x$, $n_y$ and $n_z$ represent refractive indices of light vibrating in directions of x-axis, y-axis and z-axis, respectively, and since the direction of the longitudinal axis of the liquid crystal molecule coincides with that of the z-axis, light travelling along the z-axis is an ordinary ray and light normal thereto is an extraordinary ray, namely, $n_z = n_e < n_x = n_y = n_o$.

Figure 17:
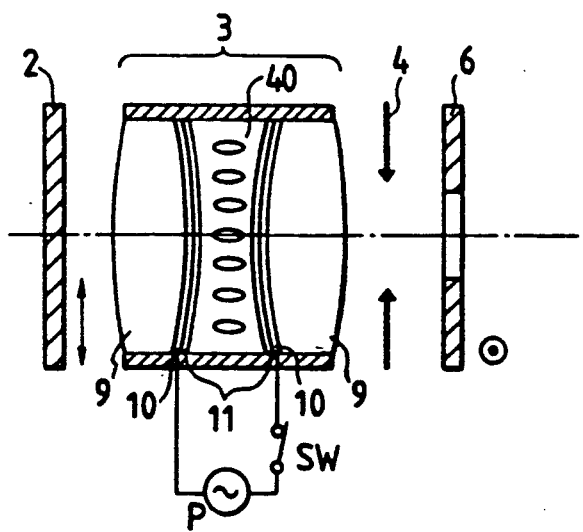

In FIG. 16, the z-axis of the molecule of the liquid cell 40 intersects perpendicularly with the optical axis and as such the refractive index of the light (extraordinary ray) traversing the liquid crystal cell of the liquid crystal lens 3 is low, which results in the state that the object at a near point is in focus. At this time, the peripheral part of the polarizing plate 6 turns to the light blocking part and the light passes through the central part. Further, in FIG. 17, since the z-axis of the molecule of the liquid crystal 40 is parallel to the optical axis, the refractive index of the light (ordinary ray) traversing the liquid crystal cell of the liquid crystal lens 3 is high, which results in the state that the object at a far point is in focus. Then, the whole of the polarizing plate 6 functions as a transparent body.

By doing so, in the case of FIG. 7 in which the opening of the stop is larger, the arrangement of the molecules of the liquid crystal 40 is regular in comparison with the case of FIG. 16 and consequently the flare is little. In the case of FIG. 16, contrary to this, the beam of light is limited, though the flare is much, and as such a thin portion of the liquid crystal cell is used, with a resultant advantage that the flare is diminished.

Figure 19:
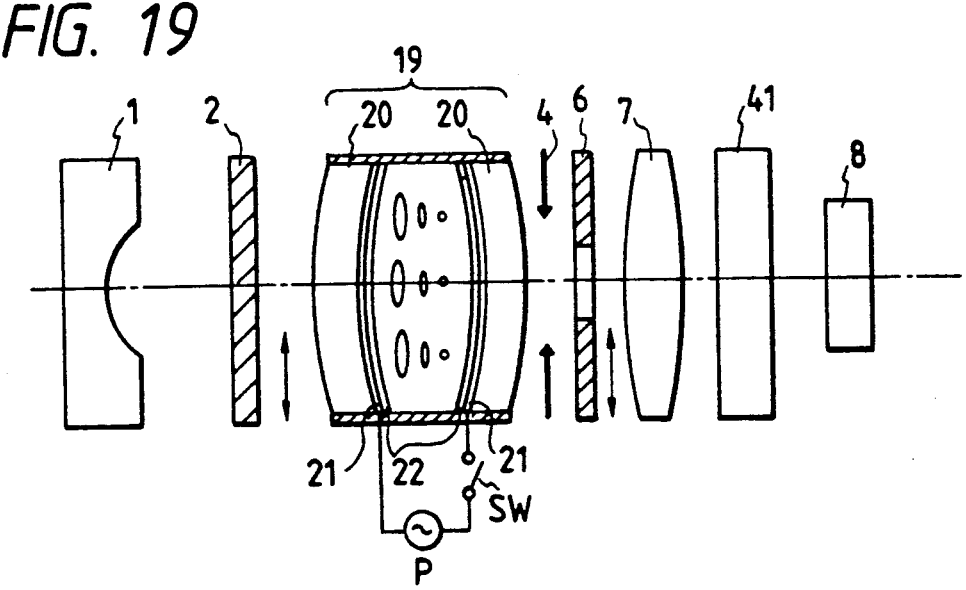
FIGS. 19 and 20 are views showing an eighth embodiment and a ninth embodiment, respectively.

FIG. 19 shows an eighth embodiment, which is provided with a birefringent plate 41 such as calcite in front of the solid-state image pickup element 8 of the second embodiment. The birefringent plate 41 is arranged so that refractive index $n_e$ is large in relation to the polarized light whose vibrating direction is parallel to the plane of the figure and refractive index $n_o$ is small in relation to the polarized light whose vibrating direction is normal to the plane of the figure. Therefore, an air conversion optical path length of the birefringent plate 41 in the state that the object at a near point is in focus is $1/n_o$ and that of the birefringent plate 41 in the state that the object at a far point is in focus is $1/n_e$. This result is equivalent to the fact that a focussing position of the solid-state image pickup element 8 is shifted by $1/n_o - 1/n_e$, so that the advantage is brought about that the difference between the far point and the near point is further made large compared with the second embodiment.

Also, if the birefringent plate 41 is provided in the position where a marginal ray is not parallel to the optical axis, it may be arranged between the lenses. Alternatively, as indicated by chain lines in FIGS. 1 and 5, the birefringent plate 41 may also be disposed in the first and third embodiments, respectively.

Figure 20:
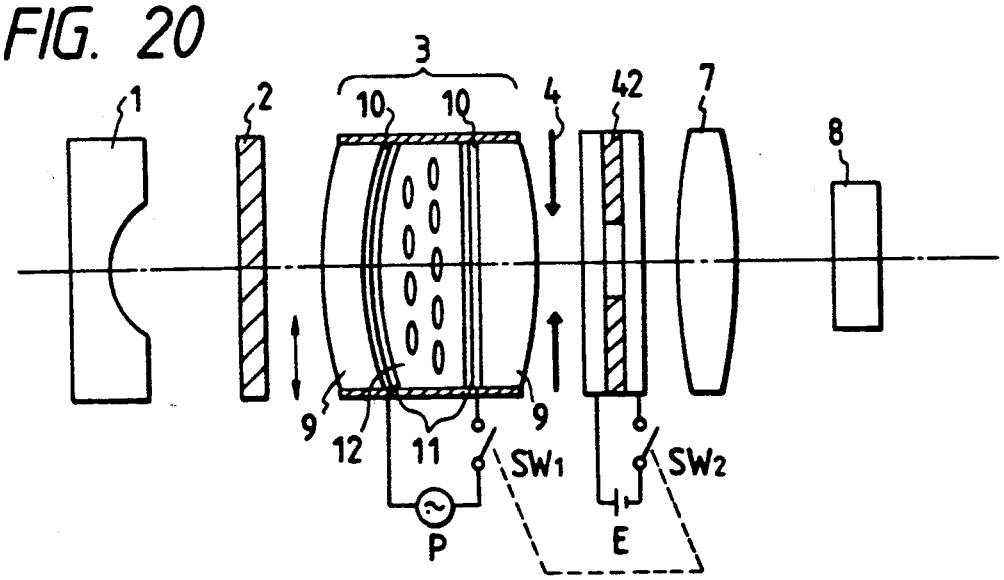

FIG. 20 shows a ninth embodiment, which is composed of a stop 42 constructed from an electrochromic element provided as a light blocking member variable in aperture size. In the case where the voltage is not applied as diagramed in this figure, the positive refracting power of the liquid crystal lens 3 is strong and the peripheral part of the stop 42 is in a light blocking state, with the result that the object at a near . point is in focus and the depth of field is increased. Contrary, in the case where the voltage is applied, the positive refracting power of the liquid crystal lens 3 is weakened and the stop 42 is fully opened, so that the object at a far point is in focus and a bright image is available.

Generally, in the fifth embodiment (FIG. 9), the sixth embodiment (FIG. 12) and the example shown in FIG. 15 which make use of liquid crystals and particularly cholesteric liquid crystals, an image may be colored by the liquid crystal. Even when the condition of the liquid crystal is changed, color sometimes varies. As such, in the case of the electronic endoscope making use of the solid-state image pickup element, designs may be made so that it is electrically corrected. Specifically, the color balance of an image pickup circuit is automatically changed in accordance with the condition of the liquid crystal to suppress the variation of color. This is accomplished by the process that the information of color in individual conditions of the liquid crystal is stored in a memory and thereby the color balance of the circuit is changed. At the same time, the coloration of the polarizing plate can also be corrected.

Although the removal of the circularly polarizing plate 28 from the sixth embodiment described above merely brings about in-focus at the near point and far point and is devoid of the effect of the stop at the near point, such is simple in structure and excellent in comparison with a variable focal length lens making use of an ordinary nematic liquid crystal.

Figure 21:
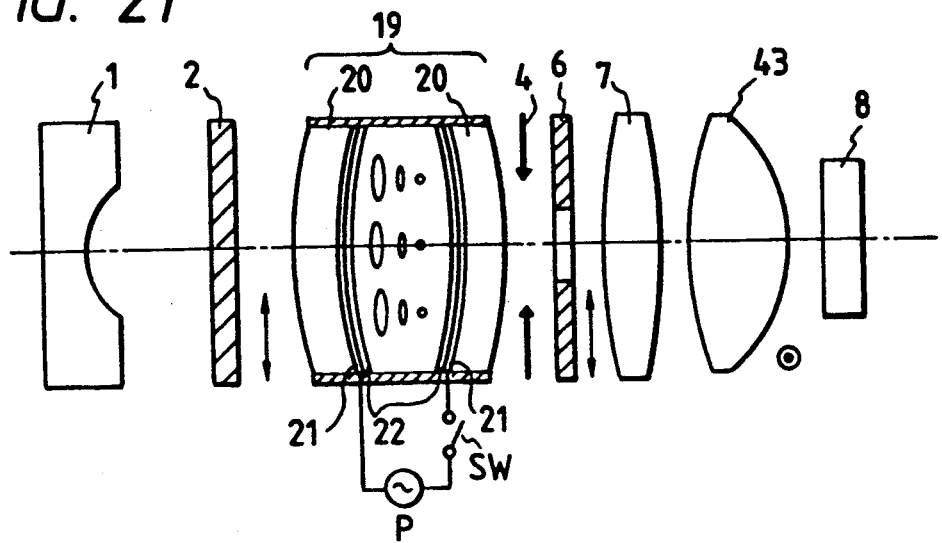
FIGS. 21, 22 and 23 are views showing a tenth embodiment, an eleventh embodiment and a twelfth embodiment, respectively.

FIG. 21 depicts a tenth embodiment, in which a lens 43 configured from birefringent materials such as calcite and liquid crystal polymer is employed instead of the birefringent plate 41 of the eighth embodiment (FIG. 19). In the lens 43, the major axis of the refractive index ellipsoid of the birefringent material is normal to the plane of the figure. The figure shows the case where the distance to the object is short and the polarized light, normal to the plane of the figure, traversing the central part of the polarizing plate 6 is intensively bent at the lens 43, so that the near point can be viewed in comparison with the eighth embodiment. When the switch SW is turned on and the voltage is applied, the polarized light travelling in parallel with the plane of the figure and in a vertical direction is incident on the birefringent lens 43, with the result that the refracting power of the lens 43 is reduced and the far point can be viewed as compared with the case of the eighth embodiment. Also, even though the power of the liquid lens 19 is made zero for the construction that the twisted nematic liquid crystal is enclosed between the parallel planes, the focus can be taken onto the solid-state image pickup element 8 due to the presence of the birefringent lens 43.

Although each of the embodiments stated above makes use of the molecule liquid crystal which is liquid as a material having an electrooptic effect, instead of this, PLZT, KDP, liquid crystal polymer and the like which are solid may be used.

Figure 22:
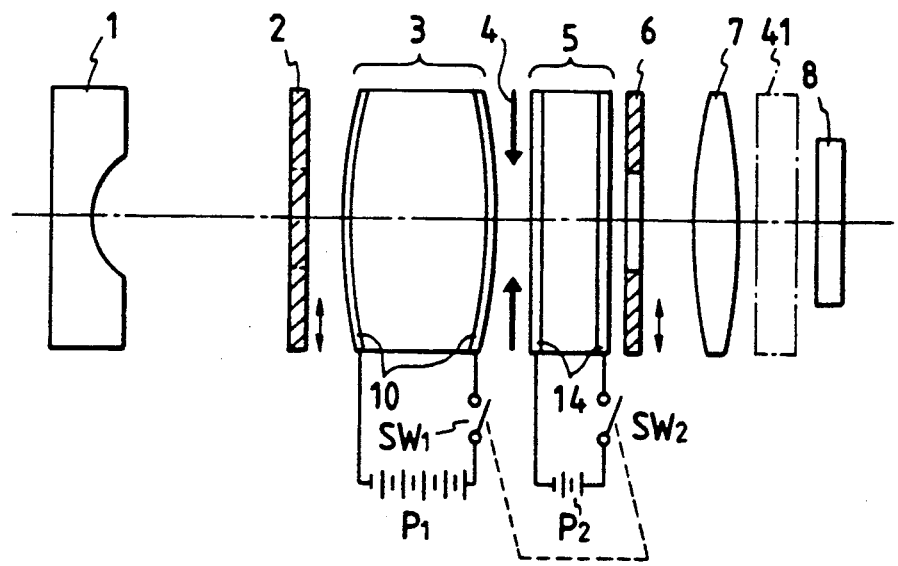

FIG. 22 shows an eleventh embodiment, which is different from the first embodiment in that both the variable focal length lens 3 and the optically active plate are made from PLZT, KDT, liquid crystal polymer and the like, in that polarizing directions of the polarizing plates 2 and 6 are the same, and in that the power sources $P_1$, $P_2$ are of direct current. When the switches $SW_1$, $SW_2$ are turned off as shown, no voltage is applied to each of the lens 3 and the optically active plate 5, so that the refracting power of the lens 3 is weak and the optically active plate 5 fails to exhibit the optical rotatory power. Since the entire optical system therefore results in the state that the object at a far point is in focus, all incident light passes through the polarizing plate 6 and a bright picture image is obtained. Contrary, when the switches $SW_1$, $SW_2$ are turned on, the voltage is applied to each of the lens 3 and the optically active plate 5, with the result that the refracting power of the lens 3 is increased and the optically active plate 5 allows its polarized plane to be rotated by an angle of 90°. Thus, since the light passing through the marginal portion of the aperture stop 4 cannot traverse the polarizing plate 6, it follows that the beam of light is limited and the picture image of the object at a near point which is large in depth of field is available.

Figure 23:
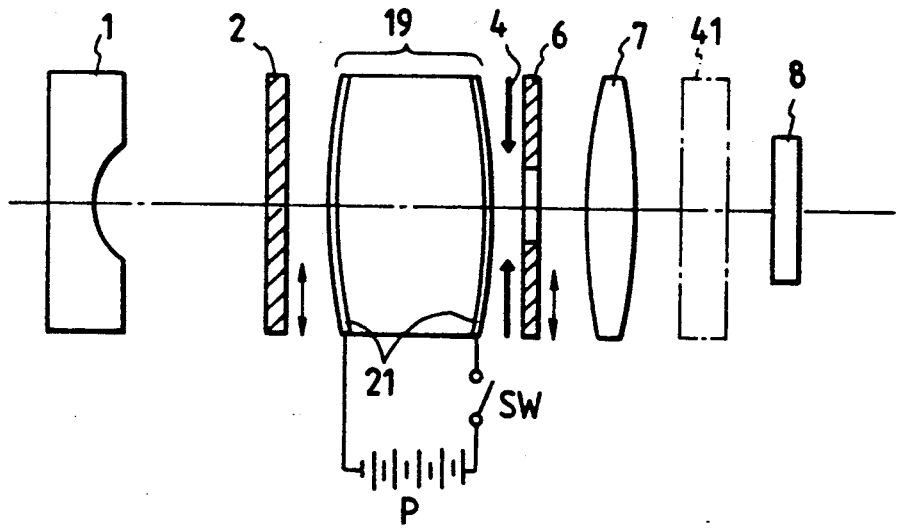

FIG. 23 shows a twelfth embodiment, which differs from the second embodiment (FIG. 3) in that the double function lens 19 is configured from PLZT, KDP, liquid crystal polymer and the like, and the explanation of its function, which is the same as in the second embodiment, is omitted.

In the eleventh embodiment and the twelfth embodiment stated above, the optical elements having electrooptic effects which are both solid allow handling to be facilitated and can favorably be employed in an imaging optical system for endoscopes.

Figure 24:
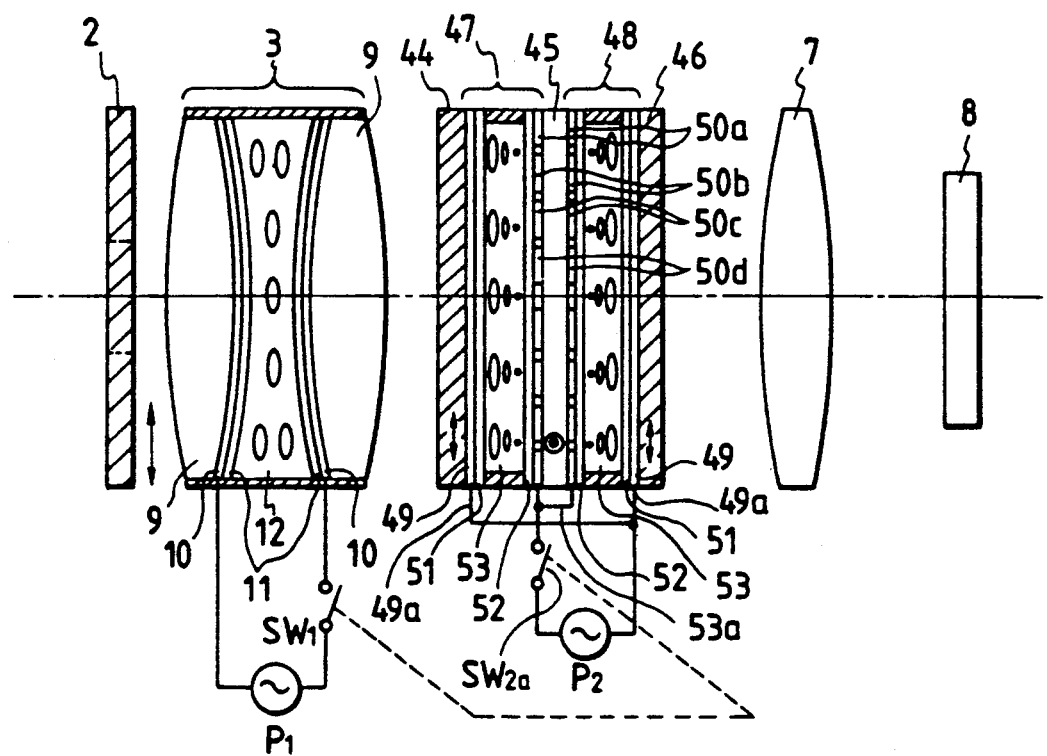
FIG. 24 is a view showing a thirteenth embodiment.
Figure 25:
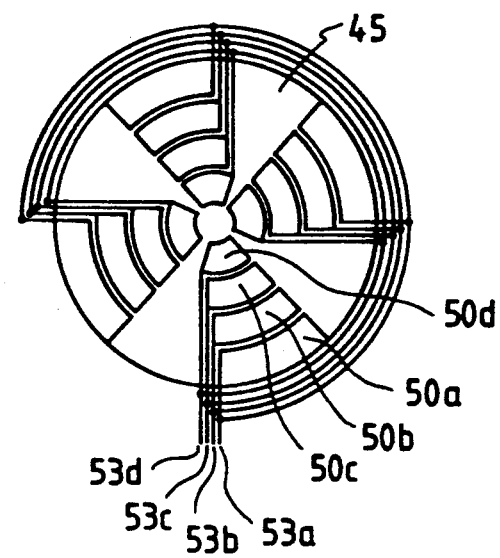
FIG. 25 is a view showing a pattern of transparent electrodes for one transparent cell constituting light blocking means used in the thirteenth embodiment.

FIGS. 24 and 25 are views showing a thirteenth embodiment and a transparent electrode pattern of one of its cells, respectively. Reference numerals 44, 45 and 46 represent polarizing plates also used as three transparent substrates in which polarizing directions intersect alternately at right angles, among which transparent cells 47 and 48 comprising first and second liquid crystals enclosed, respectively, are configured. The first liquid crystal cell 47 has a transparent electrode 49 configured on the entire surface of one of its inner sides (i.e., the inner side of the polarizing plate) and as diagrammed in FIG. 25, includes transparent electrodes 50a, 50b, 50c, 50d configured in the section corresponding to one of circumferential portions of plural concentric circles at every other segment of those virtually equally divided on the other side (i.e., the front side of the polarizing plate 45). It is, however, favorable that segments provided with the transparent electrodes are somewhat large as compared with those with no transparent electrodes. Further, on the transparent electrode 49 and the segmental transparent electrodes 50a, 50b, 50c, 50d are laminated orientation films 51 and 52 whose orientation directions coincide with the polarizing directions of the polarizing plates 44 and 45, respectively, and on the inside thereof is enclosed a nematic liquid crystal 53 which is positive in dielectric anisotropy. That is, the liquid crystal cell 47 is the twisted nematic liquid crystal cell. As depicted in FIG. 25, lead-in electrodes 53a, 53b, 53c, 53d are connected to the transparent electrodes 50a, 50b, 50c, 50d, respectively, through segments which are not provided with any electrode, and individual lead-in electrodes 53a, 53b, 53c, 53d are connected with respect to all segments. The liquid crystal cell 48 is such that the cell of the same structure as the first liquid crystal cell 47 is merely arranged in a reverse direction and the segments in which the transparent electrodes 50a, 50b, 50c, 50d are configured on the rear side of the polarizing plate 45 just cover those in which the transparent electrodes 50a, 50b, 50c, 50d of the first liquid crystal cell 47 are not provided. Further, as shown in FIG. 24, the lead-in electrodes 53a, 53b, 53c, 53d, after individually connected with respect to the first and second liquid cells 47 and 48, are connected to the power source $P_2$ through switches $SW_{2a}$, $SW_{2b}$, $SW_{2c}$, $SW_{2d}$, respectively, and a lead-in electrode 49a of the entirely transparent electrode 49, after also individually connected in relation to the first and second liquid cells 47 and 48, is connected to the power source $P_2$. Also, individually connected states of the lead-in electrodes 53b, 53c, 54d and the switches $SW_{2b}$, $SW_{2c}$, $SW_{2d}$ are not shown for certain reasons of the drawing. Thus, as is obvious from the above explanation, the individual transparent electrodes 50a, 50b, 50c, 50d of the first and second liquid cells 47 and 48 are formed with complete annular segments as a whole, which assume concentric circles.

Since the thirteenth embodiment is constructed as in the foregoing, when all the switches $SW_1$, $SW_{2a}$, $SW_{2b}$, $SW_{2c}$, $SW_{2d}$ are set at OFF as shown in FIG. 24, the liquid crystal lens 3 is in the state that the object at a far point is brought into focus as explained referring to FIG. 1 and, due to the liquid crystal molecules of the liquid crystal cells 47, 48 which assume the twist alignment, the linearly polarized light incident on the first liquid crystal cell 47 through the polarizing plate 44 traverses the polarizing plate 45 while the plane of polarization is rotated 90° by the liquid crystal cell 47 and passes through the polarizing plate 46 while the plane of polarization is further rotated 90° by the liquid crystal cell 48. At this time, therefore, the stop is in a fully opened state.

Next, when only the switch $SW_{2a}$ is set at ON, only the liquid crystal molecules of the section corresponding to the transparent electrode 50a relative to the first and second liquid crystal cells 47 and 48 turn to the homeotropic alignment and are devoid of the action rotating the plane of polarization of the linearly polarized light. As such, the linearly polarized light traversing the section corresponding to the transparent electrode 50a of the first liquid crystal cell 47 through the polarizing plate 44 cannot pass through the polarizing plate 45 and, even though the linearly polarized light traversing the section devoid of the transparent electrode 50a of the first liquid crystal cell 47 through the polarizing plate 44 can pass through the polarizing plate 45, the light then travels through the section corresponding to the transparent electrode 50a of the second liquid crystal cell 48, so that it cannot pass through the polarizing plate 46. Also, except for those sections, the light can pass through, as stated above. Thus, only the sections of the annular segments configured by the transparent electrode 50a relative to the liquid crystal cells 47 and 48 block the light and the opening of the stop in this case comes up to the inside diameter of the annular segment.

By the same principle as in the foregoing, when the switches $SW_{2a}$ and $SW_{2b}$ are ON, both the sections of two annular segments constructed by the transparent electrodes 50a and 50b of the liquid crystal cells 47 and 48 block the light so that the inside diameter of the segment configured by the transparent electrode 50b turns to the opening of the stop, while on the other hand, when the switches $SW_{2a}$, $SW_{2b}$ and $SW_{2c}$ are ON, the sections of three annular segments constructed by the transparent electrodes 50a, 50b and 50c of the liquid and 48 block the light so that the inside diameter of the segment configured by the transparent electrode 50c serves as the opening of the stop. Further, when all the switches $SW_{2a}$, $SW_{2b}$, $SW_{2c}$, $SW_{2d}$ are turned on, the sections of four annular segments constructed by all the transparent electrodes 50a, 50b, 50c, 50d of the liquid crystal cells 47 and 48 block the light and the inside diameter of the segment configured by the transparent electrode 50d turns to the opening of the stop, namely, the stop exhibits the minimum opening.

As such if the switch $SW_1$ is properly interlocked with the switches $SW_{2a}$, $SW_{2b}$, $SW_{2c}$, $SW_{2d}$ in regard to ON-OFF operation, for instance, if the switch $SW_1$ is interlocked so as to be an ON condition only when the switches $SW_{2c}$, $SW_{2d}$ are ON, three kinds of the opening of the stop can be selected in the case where the object at a far point is in focus through the liquid lens 3 and two kinds of the opening of the stop in the case where the object at a near point is in focus.

Although the opening of the stop can thus be changed into five steps, all the segments assume complete annular configurations and consequently no light leaks in the state that the light is blocked. Further, since the electrode can be extended to the outside by using segmental section devoid of the transparent electrode and its area can be made large, the structure of the lead-in electrode is simplified.

Figure 26:
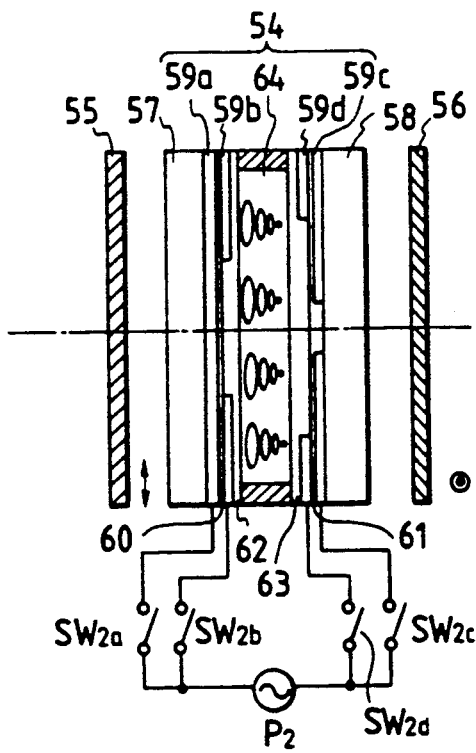
FIGS. 26 and 27 are sectional views showing the light blocking means of a fourteenth embodiment and a fifteenth embodiment, respectively.

FIG. 26 is a sectional view of a fourteenth embodiment, which is constructed from a twisted nematic liquid crystal cell 54 and two polarizing plates 55, 56 between which the liquid crystal 54 is sandwiched and whose polarizing directions are normal to each other. The liquid crystal cell 54 comprises two transparent substrates 57, 58; a transparent electrode 59a configured on the entire surface of the inner side of the transparent substrate 57; an annular transparent electrode 59b which is moderate in inside diameter, laminated through an insulating layer 60 on the transparent electrode 59a; an annular transparent electrode 59c which is small in inside diameter, configured on the inner side of the transparent substrate 58; an annular transparent electrode 59d which is large in inside diameter, laminated through an insulating layer 61 on the transparent electrode 59c; an orientation films 62, 63 laminated on the transparent electrode 59b and the insulating layer 60, and the transparent electrode 59d and the insulating layer 61, respectively, whose orientation directions are twisted by 90° each other; and a nematic liquid crystal 64 enclosed between the orientation films 62, 63 which is positive in dielectric anisotropy. The transparent electrodes 59a, 59b, 59c, 59d are arranged as concentric circles and annuluses about the optical axis, and their peripheral edges coincide with that of the liquid crystal cell 54. As well, the transparent electrodes 59a, 59b, 59c, 59d are connected to the power source $P_2$ through the switches $SW_{2a}$, $SW_{2b}$, $SW_{2c}$, $SW_{2d}$, respectively. Although, in fact, the liquid crystal lens 3 and the polarizing plate 2 are arranged on the object side of the liquid cell 54 and the lens 7 and the solid-state image pickup element 8 on the image side thereof, their figures are omitted.

This embodiment is constructed as in foregoing, so that when all the switches $SW_{2a}$, $SW_{2b}$, $SW_{2c}$, $SW_{2d}$ are set at OFF as shown in FIG. 26, the stop assumes the fully opened state in accordance with the same principle as in the thirteenth embodiment (FIG. 24). When the switches $SW_{2b}$ and $SW_{2d}$ are turned on, only the sections corresponding to the transparent electrode 59d turn to the light blocking state and the opening of the stop in this case comes up to the inside diameter of the transparent electrode 59d. Further when the switches $SW_{2b}$ and $SW_{2c}$ are set at ON, only the sections corresponding to the transparent electrode 59b block the light and the opening of the stop in this case comes up to the inside diameter of the transparent electrode 59b. In addition, when the switches $SW_{2a}$ and $SW_{2c}$ are turned on, only the sections corresponding to the transparent electrode 59c causes the light blocking state and the opening of the stop comes up to the inside diameter of the transparent electrode 59c, namely, the stop exhibits the minimum opening.

Although the opening of the stop can thus be changed into four steps by interlocking with the switch $SW_1$ in operation, in this embodiment, all the segments assume complete annular configurations and no space among the segments exists, with the result that the light does not entirely leak in the light blocking state. Further, since lead wires connected to all the electrodes can be taken out of the peripheral edge of the liquid crystal cell 54, the structure of the connection to the electrodes is simplified.

Also, the thirteenth and fourteenth embodiments stated above can be applied to not only a liquid crystal stop, but also an electrochromic stop.

Figure 27:
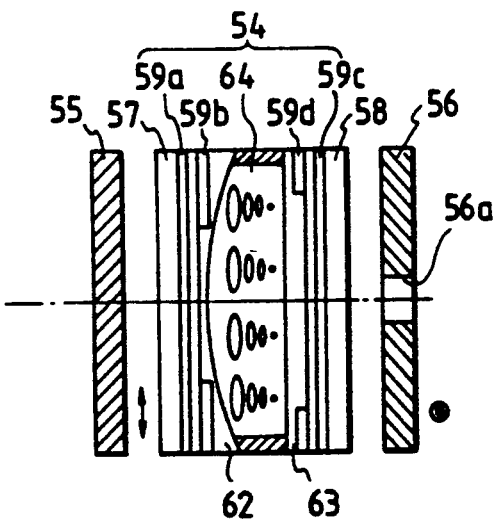

FIG. 27 is a sectional view of a fifteenth embodiment, which is constructed so that the liquid crystal cell 54 is configured like a positive lens, the transparent electrode 59c is shaped into a circular form on the entire inner side of the transparent substrate 58, and a central part 56a of the polarizing plate 56 is made into ordinary glass free from a polarizing function to be also used as a stop, and which has the same structure as the fourteen embodiment except for the preceding respects. Therefore, in this embodiment in which the central part 56a of the polarizing plate 56 has no polarizing function, only this particular part varies in refractive power when the minimum opening is brought about.

Figure 28:
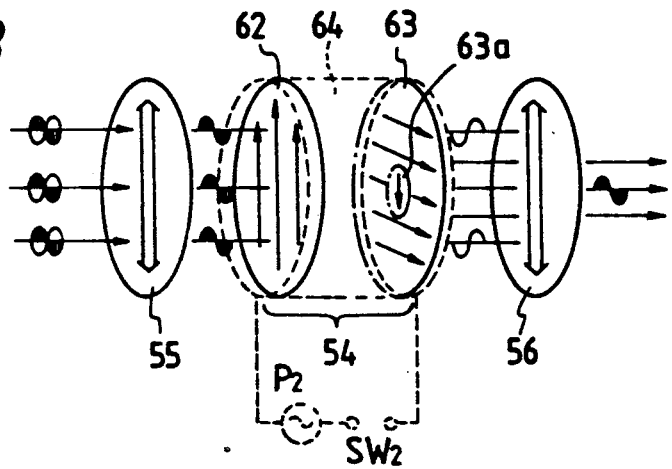
FIG. 28 is a schematic view showing a structure of the light blocking means of a sixteenth embodiment.

FIG. 28 is a schematic view of a sixteenth embodiment, in which the polarizing directions of the polarizing plates 55 and 56 coincide with each other, the orientation direction of a central part 63a of the orientation film 63 coincides with that of the orientation film 62, and the orientation direction of the other part is twisted by 90° with respect thereto. Specifically, the molecules of the liquid crystal 64 assume the homogeneous alignment in the part corresponding to the central part 63a of the orientation film 63 and the twist alignment in the other part.

This embodiment is constructed as in the foregoing, so that when the switch $SW_2$ is set to OFF as shown, light incident on the liquid crystal cell 54 through the polarizing plate 55 traverses the polarizing plate 56 because the plane of polarization is not rotated in the part corresponding to the central part 63a of the orientation film 63 and, contrary to this, in the other part, the light is blocked by the polarizing plate 56 because the plane of polarization is rotated by 90°. That is, the stop is in a stopping-down state. On the other hand, when the switch is set to ON, the molecule array of the liquid crystal 64 turns to the homeotropic alignment in all parts and, as result, the light entering the liquid crystal cell 54 through the polarizing plate 55 travels through the polarizing plate 56 since the plane of polarization is not rotated over the entire area. That is, the stop passes into the fully opened state. Hence, in this embodiment, interlocking operation is performed so that when the switch $SW_1$ (not shown) is OFF, the switch $SW_2$ is set at ON and when the switch $SW_1$ is ON, the switch $SW_2$ is set at OFF.

The opening of the stop can thus be changed into two steps and in order to secure two areas of different orientation directions, it is only necessary to apply twice the orientation treatment (rubbing treatment and the like) in different directions to the orientation film 63 and cover partially a treating surface by means of a mask in the second treatment, with resultant advantages that the structure of the embodiment is much simple in comparison with a process of fabricating the transparent electrode as in the thirteenth to the fifteenth embodiments and is low in manufacturing cost.

Figure 29:
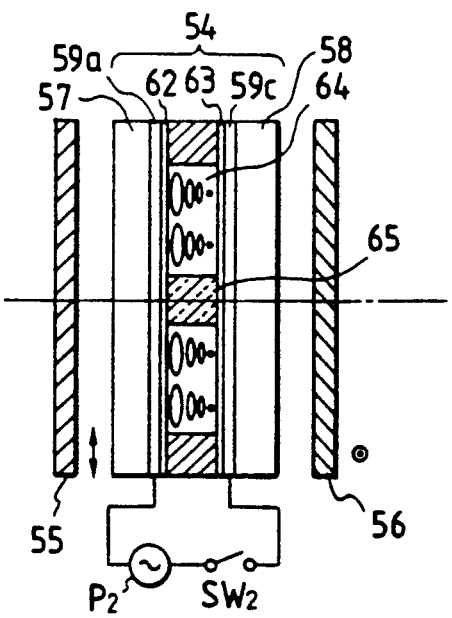
FIG. 29 is a sectional view showing the light blocking means of a seventeenth embodiment.

FIG. 29 is a sectional view of a seventeenth embodiment, in which a cylindrical transparent member 65 is disposed in the central portion of the liquid crystal cell 54.

This embodiment is constructed as in the foregoing, so that when the switch $SW_2$ is OFF, light incident on the liquid crystal cell 54 through the polarizing plate 55 traverses the polarizing plate 56 because the plane of polarization is not rotated in the area of the transparent member 65, while in the area of the liquid crystal 64, the light is blocked by the polarizing plate 56 because the plane of polarization is rotated by 90°. That is, the stop is in the stopping-down state. On the other hand, when the switch $SW_2$ is set to ON, the molecules of the liquid crystal 64 assume the homeotropic alignment and consequently all the light incident on the liquid crystal cell 54 through the polarizing plate 55 traverses the polarizing plate 56 since the plane of polarization is not rotated over the entire area. That is, the stop turns to the fully opened state.

The opening of the stop can thus be changed into two steps and a transparent adhesive mixed with a material for gap control may be used as the transparent member 65, thereby bringing about the same effect as the case where a spacer is provided in the central part of the liquid crystal cell 54.

Figure 30:
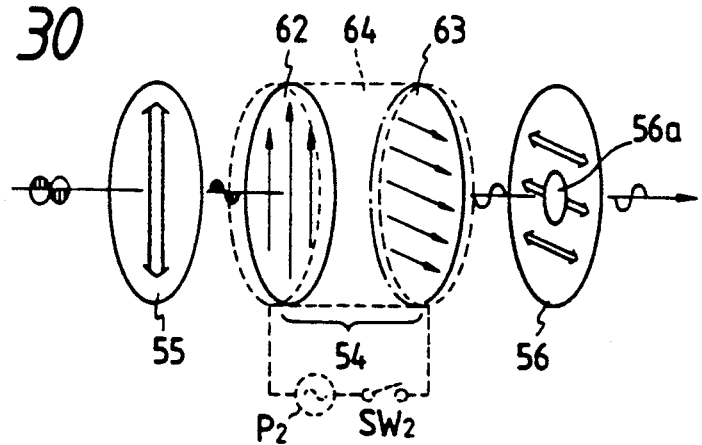
FIG. 30 is a schematic view showing a structure of the light blocking means of an eighteenth embodiment.

FIG. 30 is a schematic view of an eighteenth embodiment, which is constructed so that the polarizing directions of the polarizing plates 55 and 56 are twisted by 90° each other and the central part 56a of the polarizing plate 56 is made into ordinary glass devoid of the polarizing function. Also, the orientation directions of the orientation films 62, 63 are as shown by arrows.

This embodiment is constructed as stated now, so that when the switch $SW_2$ is OFF as shown, light incident on the liquid crystal cell 64 through the polarizing plate 55 passes through the entire area of the polarizing plate 56 because the plane of polarization is rotated by 90°. That is, the stop is in the fully opened state. In contrast to this, when the switch is turned on, the molecules of the liquid crystal 64 assume the homeotropic alignment, with the result that the light entering the liquid crystal cell 54 through the polarizing plate 55 traverses the central part 56a of the polarizing plate 56, but is blocked by the other part. That is, the stop turns to the stopping-down state.

Figure 31:
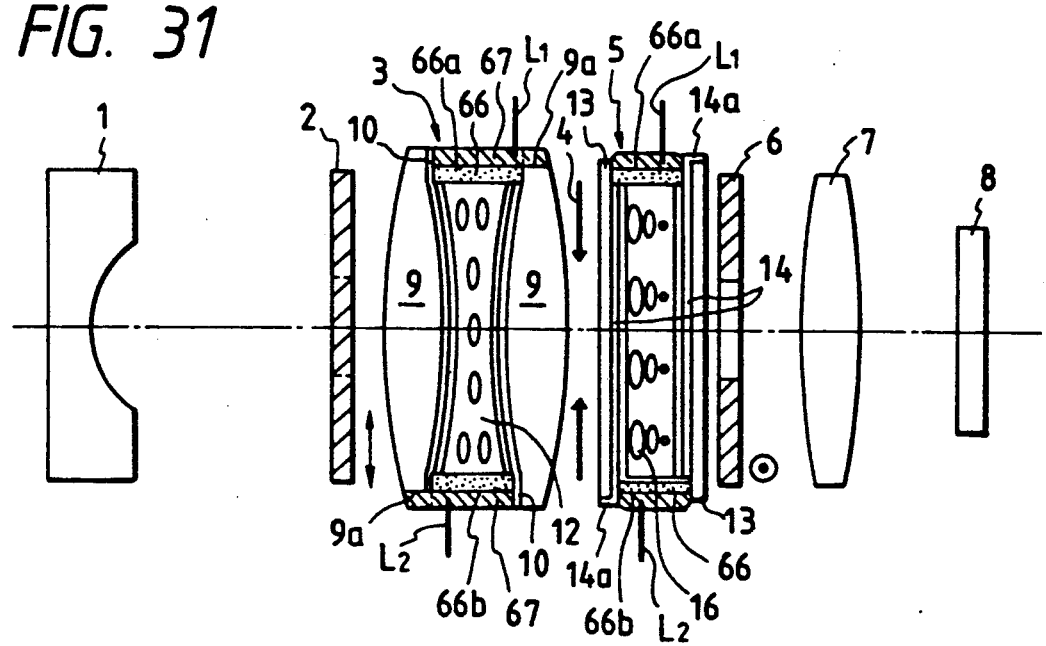
FIGS. 31, 32A and 32B are views showing a nineteenth embodiment.

FIGS. 31, 31A and 31B show a nineteenth embodiment. This embodiment is characterized by the structure of the connection between lead wires $L_1$, $L_2$ for connecting the transparent electrodes 10, 10 of the liquid crystal lens 3 to the power source $P_1$ as well as the switch $SW_1$ and the electrodes 10, 10 and the structure of the connection between lead wires $L_1$, $L_2$ for connecting the transparent electrodes 14, 14 of the optically active plate 5 to the power source $P_2$ as well as the switch $SW_2$ and the electrodes 14, 14. Specifically, the lenses 9, 9 in which the transparent electrodes 10, 10 and the orientation films 11, 11 are laminated on their inner surfaces positioned opposite to each other face mutually through an annular spacer 66 with electrical insulation characteristics and as clearly shown in FIG. 32A, cutting portions 66a, 66b are formed at opposite peripheral edges of the spacer 66. On the circumference of the one lens 9 (a right-hand lens in FIG. 31) corresponding to the cutting portion 66a is configured a cutting portion 9a with the same shape, and the end of the transparent electrode 10 provided on the other lens 9 (a left-hand lens in FIG. 31) comes into the cutting portion 66a. Further, a conductive adhesive 67 prepared from silver paste and the like is charged in each of the cutting portions 9a, 66a. As such, in the case where the adhesive 67 is charged, if, for example, an end of the lead wire $L_1$ is inserted into the cutting portion 66a, the transparent electrode 10 of the other lens 9 and the lead wire $L_1$ will electrically be connected through the adhesive 67 to each other. On the other hand, the cutting portion 9a assuming the same shape is configured on the circumference of the other lens 9 corresponding to the cutting portion 66b and the transparent electrode 10 provided on the one lens 9 penetrates into the cutting portion 66b. Thus, if an end of the lead wire $L_2$ is inserted into the cutting portion 66b to charge the conductive adhesive 67 therein, the transparent electrode 10 of the one lens 9 and the lead wire $L_2$ will electrically be connected through the adhesive 67 to each other. The cutting portions 66a, 66b can be each configured at a proper position of the periphery of a space for accommodating the liquid crystal and, in any case, each of them is merely provided in a portion of the periphery, so that an optical behavior of the liquid crystal will not be blocked and the connection between the transparent electrode 10 and the lead wires $L_1$ and $L_2$ will fail to protrude from the peripheral edge of the liquid crystal lens 3. As a consequence of the foregoing, if such connecting structure is adopted, the work is relatively facilitated even in the case where this particular imaging optical system is incorporated in an extremely narrow space as in the endoscope.

Figure 32A:
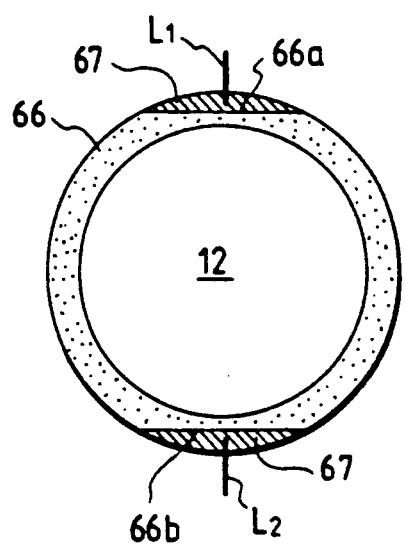
Figure 32B:
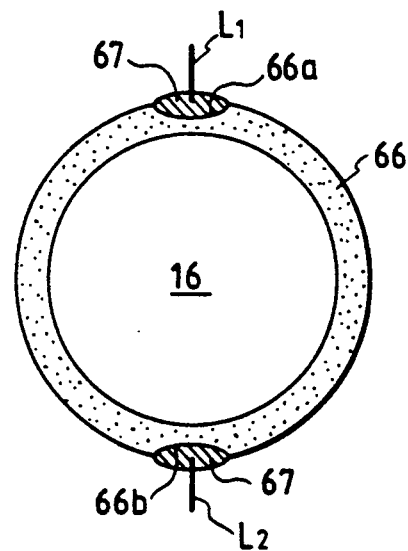

FIG. 32B shows the connecting structure somewhat different from that of FIG. 32A, which is applied to the optically active plate 5. Specifically, two transparent plates 13, 13 which are identical in diameter and virtually circular are made to face each other through the annular spacer 66 with electrical insulation characteristics and the liquid crystal 16 is charged in an airspace surrounded with the spacer 66 and the transparent plates 13, 13. A pair of cutting portions 66a, 66b is configured in portions of the circumference of the spacer 66, and extensions 14a, 14a of the transparent electrodes 14, 14 penetrate into the cutting portions 66a, 66b correspondingly. Further, the conductive adhesive 67 prepared from silver paste and the like is charged in each of the cutting portions 66a, 66b. As such, the conductive adhesive 67 comes in electrical contact with the extension 14a of the transparent electrode 14 to configure the connection connecting each of the lead wires $L_1$, $L_2$ for applying the voltage to the electrode 14. In this modified example, although the conductive adhesive 67 somewhat protrudes beyond the peripheral surface of the spacer 66, the protrusion is slight in comparison with the size of the cutting portions 66a, 66b and the periphery assumes substantially a circular configuration, so that the same advantages as in the structural example shown in FIG. 32A are brought about.

Figure 33:
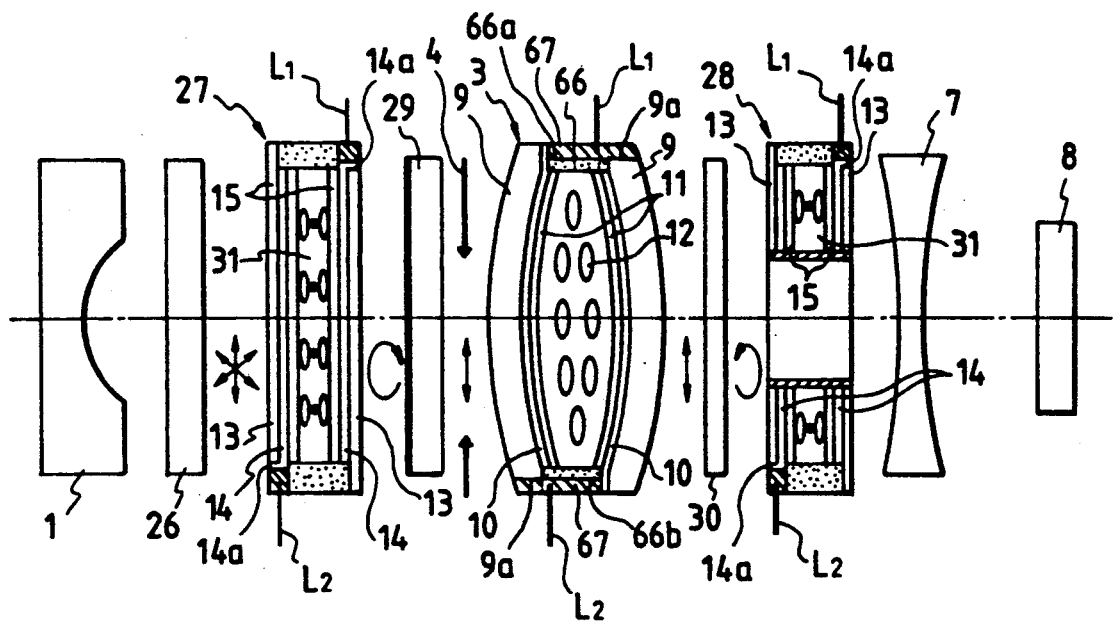
FIGS. 33, 34A and 34B are views showing a twentieth embodiment.
Figure 34A:
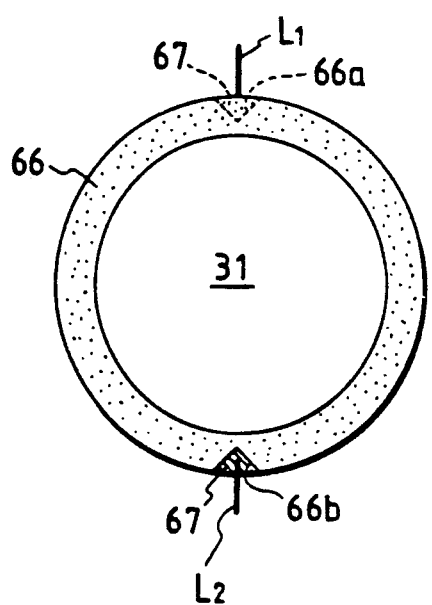
Figure 34B:
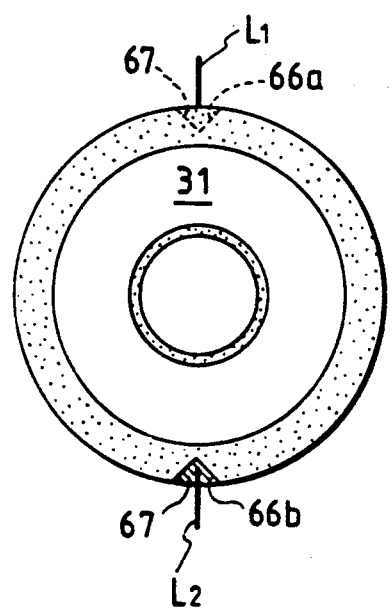

FIGS. 33, 34A and 34B show a twentieth embodiment. This embodiment, like the nineteenth embodiment, is characterized by the structure of the connection between the lead wires $L_1$, $L_2$ for connecting the transparent electrodes 14, 14; 14, 14 of the circularly polarizing plates 27, 28 to the corresponding power sources and switches and the transparent electrodes. Although this embodiment has the same connecting structure as in the nineteenth embodiment with respect to the liquid crystal lens 3, it is different from the nineteenth embodiment in that the cutting portions 66a, 66b are configured in only the transparent plates 13, 13 in regard to the circularly polarizing plates 27, 28 so that the cutting portions assume V-shaped forms as depicted in FIGS. 34A and 34B and the extensions 14a, 14a of the corresponding transparent electrodes 14, 14 penetrate into the spaces of the cutting portions 66a, 66b. Also, while the embodiment has the same advantages as stated in connection with the nineteenth embodiment, due to the fact that the cutting portions 66a, 66b are configured in only the transparent plates 13, 13, the embodiment possesses the features that working and assembly are easier and an effective diameter of the space for accommodating the liquid crystal 31 can be increased.

The structure of the connection between the electrodes and the lead wires, explained above, is not limited to the preceding embodiments and can properly be selected in accordance with the structure of liquid crystal optical means.

Figure 35:
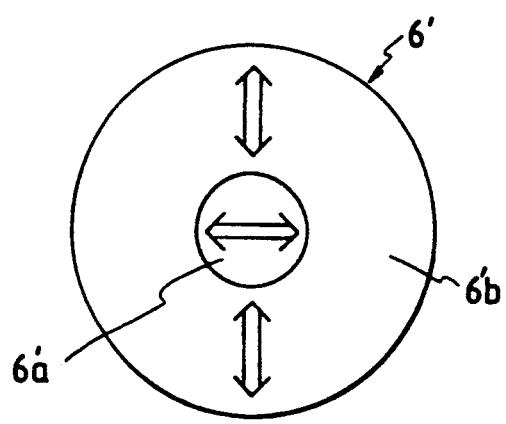
FIG. 35 is a front view showing a modified example of a polarizing plate which is a component of the light blocking means.

FIG. 35 shows a modified example of the polarizing plate 6. That is, the polarizing plate 6 in each of the embodiments shown in FIGS. 1, 3, 5, 8, 11, 16, 19, 21, 22, 23 and 31 is such that its central part is configured as a light transmitting part, while in a polarizing plate 6' shown in FIG. 35, its central part 6'a is covered with a polarizing plate selected so that the planes of 5 polarization are normal to each other with respect to a peripheral part 6'b. For this reason, in the case where the vibration of incident light travels in the direction of arrows shown in the peripheral part 6'b, the amount of light is reduced since the light of the part corresponding to the central part 6'a is blocked, in comparison with the case where the central part is constructed as the light transmitting part. This, however, does not virtually cause problems because the area of the central part 6'a is relatively small. Accordingly, the polarizing plate 6 in each of the above embodiments may be replaced by the polarizing plate 6' shown in FIG. 35.

What is claimed is:

1. An imaging apparatus having electrooptic devices, comprising:

first and second circularly polarizing means having first and second states of operation and disposed on an optical axis, said first and second circularly polarizing means in spaced relation having a space therebetween, in said first state circularly polarized light of one direction is transmitted and in said second state all circularly polarized light is transmitted;

first and second ¼ wave plates disposed on said optical axis in said space between said first and second circularly polarizing means;

a variable focal length lens containing a material having an electrooptic effect, disposed on said optical axis between said first and second ¼ wave plates;

a light blocking member having an aperture on said optical axis; and power source means for actuating in synchronization said first and second circularly polarizing means and said variable focal length lens, one of said first and second circularly polarizing means being provided with a central transparent part smaller in diameter than said aperture of said light blocking member, said first circularly polarizing means, said first ¼ wave plate, said light blocking member, said second ¼ wave plate and said second circularly polarizing means functioning as light blocking means for changing an aperture thereof to different sizes.

2. An imaging apparatus having electrooptic devices, comprising:

circularly polarizing means having two states of operation, in a first state circularly polarized light of one direction is transmitted and in a second state all circularly polarized light is transmitted;

a polarizing plate spaced away from said circularly polarizing means;

a variable focal length lens containing a material having an electrooptic effect and disposed on an optical axis between said circularly polarizing means and said polarizing plate;

a ¼ wave plate disposed on said optical axis between said variable focal length lens and said circularly polarizing means;

a light blocking member having an aperture on said optical axis; and power source means for actuating in synchronization said circularly polarizing means and said variable focal length lens, one of said circularly polarizing means and said polarizing plate being provided with a center area smaller in diameter than said aperture of said light blocking member, said circularly polarizing means, said ¼ wave plate, said light blocking means and said polarizing plate functioning as light blocking means for changing an aperture thereof to different sizes.

3. An imaging apparatus having electrooptic devices, comprising:

a variable focal length lens containing a material having an electrooptic effect and having two states different in refracting power for transmitting all light in one state and only circularly polarized light in a first direction in another state;

a light blocking member having an aperture in a central area thereof;

circularly polarizing means, having a light transmitting part at a center thereof, and two states of operation, in a first state only circularly polarized light in a direction opposite to said first direction is transmitted and in a second state all circularly polarized light is transmitted; and power source means for actuating in synchronization said variable focal length lens and said circularly polarizing means.

4. An imaging apparatus according to any one of claim 1, 2, or 3, wherein said variable focal length lens is a liquid crystal lens containing a liquid crystal enclosed in a transparent cell.

5. An imaging apparatus according to claim 4, wherein one of both sides of said transparent cell is configured as a stepwise Fresnel lens-shaped surface.

6. An imaging apparatus according to claim 4, wherein said liquid crystal lens comprises a pair of lens elements facing each other through a spacer with electrical insulation characteristics, transparent electrodes provided on inner surfaces, facing each other, of said pair of lens elements, and the liquid crystal charged in the cell produced by said spacer and said pair of lens elements, wherein cutting portions are configured in at least one of each of said lens elements and said spacer, and wherein lead wires for applying voltages to said transparent electrodes and connections with said transparent electrodes are constructed in said cutting portions.

7. An imaging apparatus according to claim 6, wherein an opaque member is provided in a surface of one of said transparent electrode on an object side of said lens, of a transparent electrode on an image side of said lens, on an image side of said liquid crystal lens, and on the object side of said circularly polarizing means.

8. An imaging apparatus according to claim 4, wherein said circularly polarizing means comprises a pair of transparent plates facing each other through a spacer with electrical insulation characteristics, transparent electrodes provided on inner surfaces, facing to each other, of said pair of transparent plates, and the liquid crystal charged in the cell produced by said spacer and said pair of transparent plates, cutting portions are configured in at least one of each of said transparent plates and said spacer, and lead wires for applying voltages to said transparent electrodes and connections with said transparent electrodes are constructed in said cutting portions.

9. An imaging apparatus according to claim 5, wherein said circularly polarizing means comprises a pair of transparent plates facing to each other through a spacer with electrical insulation characteristics, transparent electrodes provided on inner surfaces, facing to each other, of said pair of transparent plates, and the liquid crystal charged in the cell produced by said spacer and said pair of transparent plates, cutting portions are configured in at least one of each of said transparent plates and said spacer, and lead wires for applying voltages to said transparent electrodes and connections with said transparent electrodes are constructed in said cutting portions.

10. An imaging apparatus according to claim 7, wherein said circularly polarizing means comprises a pair of transparent plates facing to each other through a spacer with electrical insulating characteristics, transparent electrodes provided on inner surfaces, facing to each other, of said pair of transparent plates, and the liquid crystal charged in the cell produced by said spacer and said pair of transparent plates, cutting portions are configured in at least one of each of said transparent plates and said spacer, and lead wires for applying voltages to said transparent electrodes and connections with said transparent electrodes are constructed in said cutting portions.

11. An imaging apparatus according to claim 2, further comprising a birefringent plate disposed on said optical axis and located on an image side of said polarizing plate.

12. An imaging apparatus according to claim 2, wherein said central area of said polarizing plate is transparent.

13. An imaging apparatus according to claim 2, wherein said central area of said polarizing plate has a polarizing direction different from that of an area outside said central area.

14. An imaging apparatus according to claim 7, wherein said central area of said polarizing plate has a polarizing direction different from that of an area outside said central area.

* * * * *